(12) United States Patent
Enderby

(10) Patent No.: US 9,144,514 B2
(45) Date of Patent: Sep. 29, 2015

(54) LACTATION AID AND SOOTHING GARMENT

(71) Applicant: Christine L. Enderby, Portland, OR (US)

(72) Inventor: Christine L. Enderby, Portland, OR (US)

( * ) Notice: Subject to any disclaimer, the term of this patent is extended or adjusted under 35 U.S.C. 154(b) by 234 days.

(21) Appl. No.: 13/732,399

(22) Filed: Jan. 1, 2013

(65) Prior Publication Data

US 2014/0188199 A1 Jul. 3, 2014

(51) Int. Cl.
*A61F 7/02* (2006.01)
*A61F 7/08* (2006.01)
*A61F 7/10* (2006.01)
*A61M 1/06* (2006.01)
*A61F 7/00* (2006.01)

(52) U.S. Cl.
CPC ... *A61F 7/08* (2013.01); *A61F 7/02* (2013.01); *A61F 7/10* (2013.01); *A61M 1/06* (2013.01); *A61F 2007/0021* (2013.01); *A61F 2007/0204* (2013.01); *A61F 2007/0207* (2013.01); *A61F 2007/0225* (2013.01); *A61F 2007/0228* (2013.01); *A61F 2007/0231* (2013.01); *A61F 2007/0242* (2013.01); *A61F 2007/0273* (2013.01); *A61F 2007/108* (2013.01); *A61M 2209/08* (2013.01)

(58) Field of Classification Search
CPC ......... A61F 7/00; A61F 7/02; A61F 2007/00; A61F 2007/02; A61F 2007/0021; A61F 2007/0228; A61F 2007/0231; A61F 2007/108; A61F 7/08; A61F 7/10; A61F 2007/0225; A61F 2007/0273; A41D 23/00; A41D 15/00; A41D 1/22; A41D 13/0053; A41D 1/205; A41D 3/00; A61M 1/06; A61M 2209/08

USPC .......... 450/37, 36, 56, 1, 38, 28, 10, 30, 106, 450/105, 128, 109, 55, 57, 58; 607/108, 607/114, 139

See application file for complete search history.

(56) References Cited

U.S. PATENT DOCUMENTS

| | | | | |
|---|---|---|---|---|
| 1,620,335 A | * | 3/1927 | Farkas | 450/1 |
| 2,891,544 A | * | 6/1959 | London | 604/379 |
| 2,908,275 A | * | 10/1959 | May | 450/1 |
| 4,335,728 A | * | 6/1982 | Fildan | 450/36 |
| 4,462,224 A | * | 7/1984 | Dunshee et al. | 62/530 |
| 4,575,097 A | * | 3/1986 | Brannigan et al. | 607/112 |
| 4,908,893 A | * | 3/1990 | Smit | 5/644 |
| 5,304,215 A | * | 4/1994 | MacWhinnie et al. | 607/108 |
| RE34,883 E | * | 3/1995 | Grim | 602/13 |
| 5,441,534 A | * | 8/1995 | MacWinnie et al. | 607/108 |
| 5,522,892 A | * | 6/1996 | Lin | 623/7 |
| 5,679,052 A | * | 10/1997 | Rucki | 450/57 |

(Continued)

FOREIGN PATENT DOCUMENTS

DE 202009015364 U1 6/2010

*Primary Examiner* — Linda Dvorak
*Assistant Examiner* — Yasamin Ekrami
(74) *Attorney, Agent, or Firm* — Mersenne Law

(57) ABSTRACT

A hands-free lactation aid and soothing garment can be used for simultaneous warm and cool therapy. Therapeutic cozies can be used in conjunction with a camisole or nursing camisole, bra, or nursing bra or apparel, can be inserted into a cozy cover for use with an adjustable neckband. With the appropriate breast cozies, breast pumping or nursing can occur simultaneously with warm/cool therapy, and a privacy shield attaches easily. An additional neck therapy insert can be used to sooth a sore neck, while an additional nipple soother can be attached to the center of the cozies to provide simultaneous warm and cold therapy to the effected area.

4 Claims, 24 Drawing Sheets

(56) References Cited

U.S. PATENT DOCUMENTS

| | | | | |
|---|---|---|---|---|
| 5,683,286 A * | 11/1997 | Kielland | | 450/37 |
| 5,769,688 A * | 6/1998 | Holliday | | 450/57 |
| 5,843,062 A * | 12/1998 | Reidmiller | | 604/378 |
| 5,890,487 A * | 4/1999 | Kimmel | | 128/845 |
| 5,897,580 A * | 4/1999 | Silver | | 607/108 |
| 6,063,110 A * | 5/2000 | Stedman | | 607/108 |
| 6,110,156 A * | 8/2000 | Mendonca | | 604/345 |
| 6,241,715 B1 * | 6/2001 | Houser et al. | | 604/385.07 |
| 6,319,092 B1 * | 11/2001 | Leyhe et al. | | 450/36 |
| 6,524,331 B1 * | 2/2003 | Kohout et al. | | 607/96 |
| 6,540,585 B1 * | 4/2003 | Lee | | 450/38 |
| D485,363 S * | 1/2004 | Martin | | D24/206 |
| 6,814,647 B1 * | 11/2004 | Huang | | 450/38 |
| 6,945,966 B2 * | 9/2005 | Mikami | | 604/346 |
| 7,081,034 B1 * | 7/2006 | Zoellner | | 450/54 |
| 7,089,617 B1 * | 8/2006 | Lauro | | 5/636 |
| 7,309,275 B1 * | 12/2007 | Morales | | 450/38 |
| 7,942,722 B2 * | 5/2011 | Tseng | | 450/38 |
| 8,167,924 B2 * | 5/2012 | Rosenbaum | | 607/108 |
| 8,317,569 B2 * | 11/2012 | Fisher-Pacheco | | 450/79 |
| 8,469,769 B2 * | 6/2013 | Hendrickson | | 450/30 |
| 8,721,700 B2 * | 5/2014 | Stuffel | | 607/111 |
| 2001/0018605 A1 * | 8/2001 | Helming | | 607/108 |
| 2003/0023291 A1 * | 1/2003 | Hanner | | 607/108 |
| 2003/0150890 A1 * | 8/2003 | Perricone | | 224/148.6 |
| 2003/0186617 A1 * | 10/2003 | Sorensen | | 450/37 |
| 2003/0236053 A1 * | 12/2003 | Martz | | 450/39 |
| 2005/0070980 A1 * | 3/2005 | Noonan | | 607/108 |
| 2005/0075706 A1 * | 4/2005 | Mayrhofer et al. | | 607/96 |
| 2006/0154566 A1 | 7/2006 | Nunez | | |
| 2008/0307580 A1 * | 12/2008 | Spitzer | | 5/636 |
| 2009/0062702 A1 * | 3/2009 | Sojka et al. | | 602/2 |
| 2009/0198311 A1 * | 8/2009 | Johnson et al. | | 607/109 |
| 2010/0048098 A1 | 2/2010 | Rosario | | |
| 2010/0058538 A1 * | 3/2010 | Rieber | | 5/644 |
| 2010/0298914 A1 * | 11/2010 | Rosenbaum | | 607/108 |
| 2011/0073225 A1 * | 3/2011 | Pace et al. | | 150/105 |
| 2011/0081826 A1 * | 4/2011 | Hendrickson | | 450/36 |
| 2011/0289687 A1 * | 12/2011 | Rieber | | 5/636 |
| 2012/0071955 A1 * | 3/2012 | Yockel | | 607/114 |
| 2012/0083863 A1 * | 4/2012 | Gillespie | | 607/108 |
| 2012/0171930 A1 * | 7/2012 | Kaufman | | 450/58 |
| 2012/0259303 A1 * | 10/2012 | Carter | | 604/385.01 |
| 2012/0302135 A1 * | 11/2012 | Solotoff | | 450/52 |
| 2013/0273809 A1 * | 10/2013 | Turk et al. | | 450/36 |
| 2013/0291272 A1 * | 11/2013 | Bourque | | 2/9 |
| 2013/0326815 A1 * | 12/2013 | Smart-Thomas | | 5/636 |
| 2014/0090169 A1 * | 4/2014 | Sclare et al. | | 5/421 |
| 2014/0109318 A1 * | 4/2014 | Loos | | 5/644 |
| 2014/0154949 A1 * | 6/2014 | Pagnon | | 450/57 |

\* cited by examiner

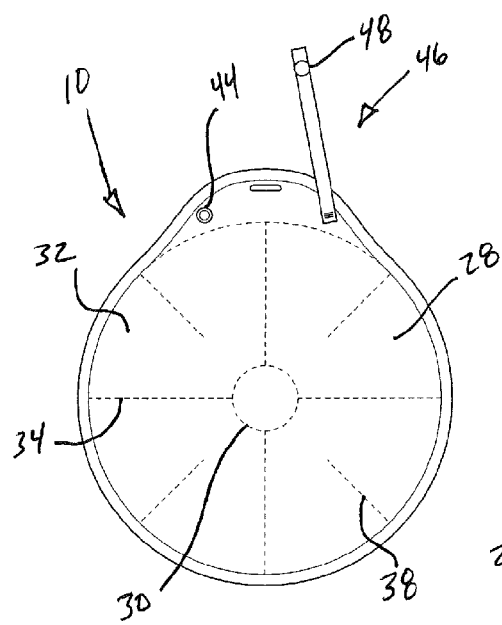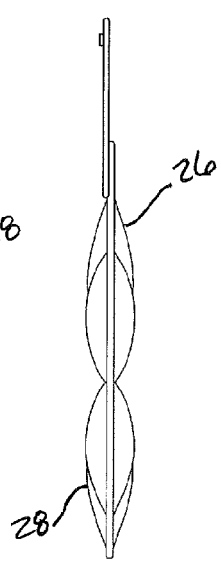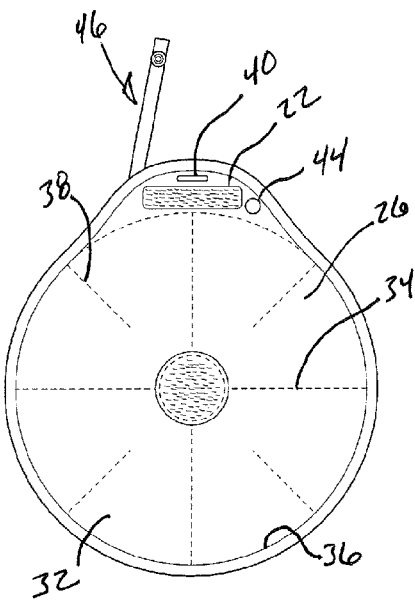
FIG. 8  FIG. 9  FIG. 10
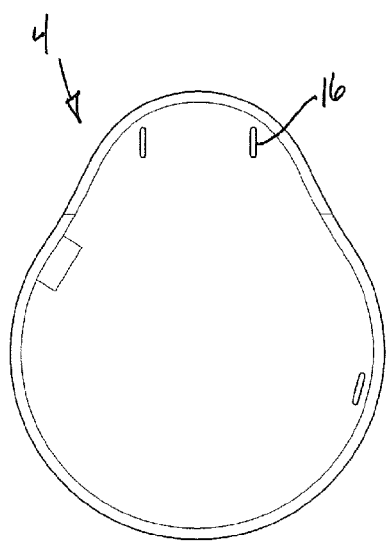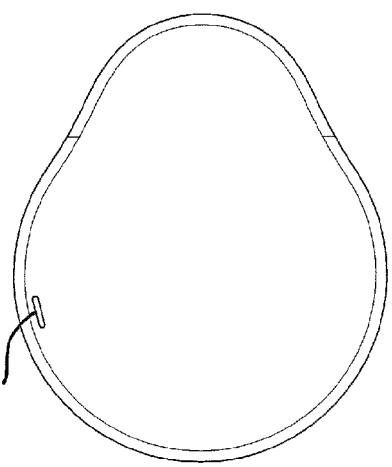
FIG. 11  FIG. 12  FIG. 13

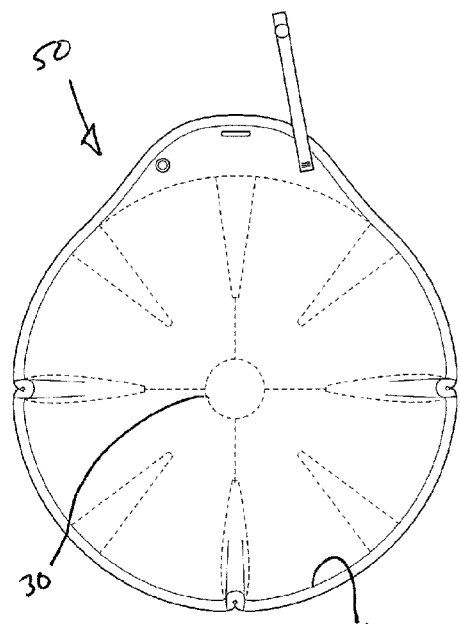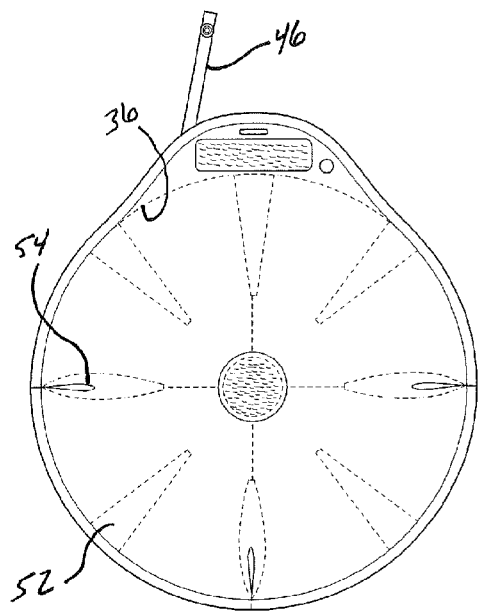
FIG. 14　　FIG. 15　　FIG. 16
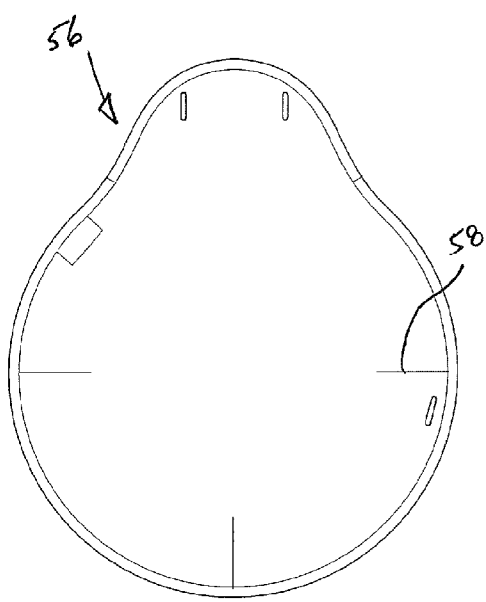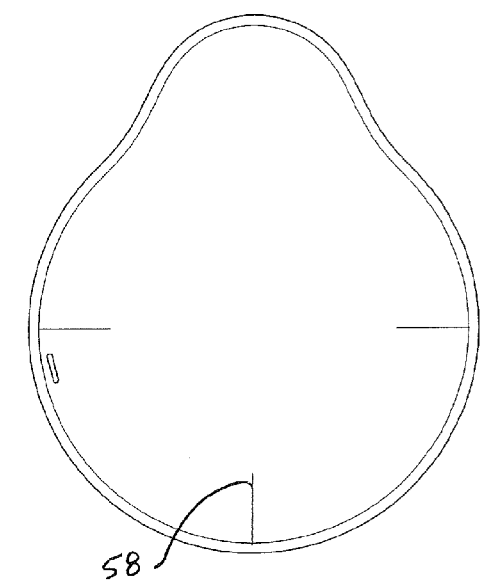
FIG. 17　　FIG. 18　　FIG. 19

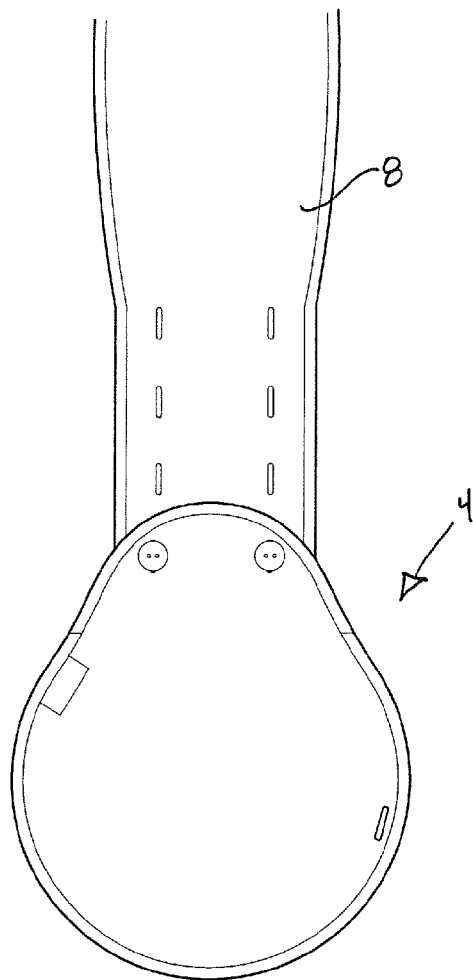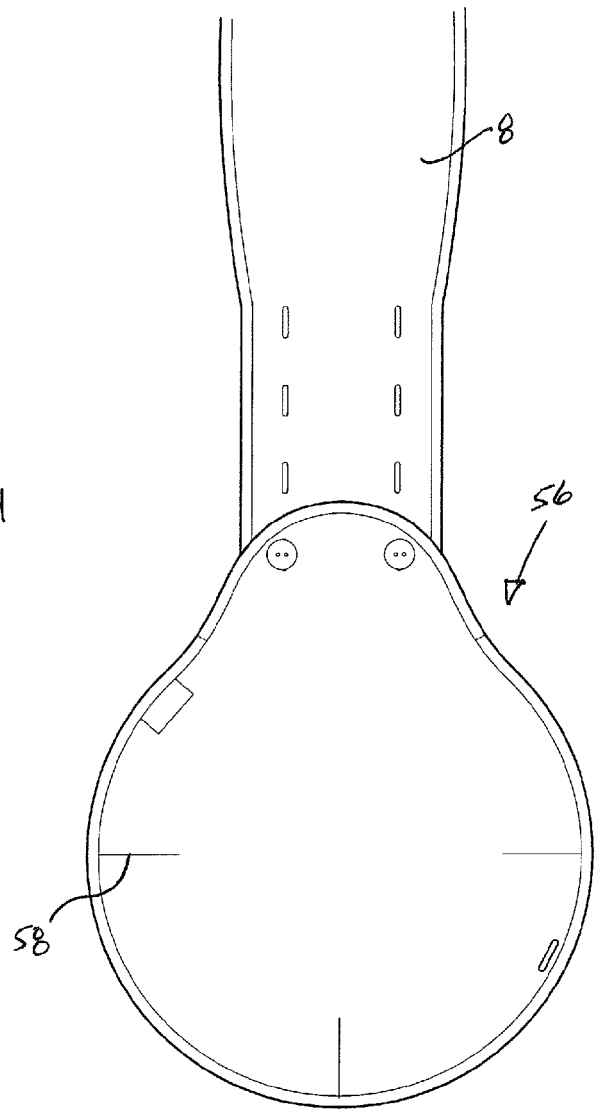
FIG. 24
FIG. 25

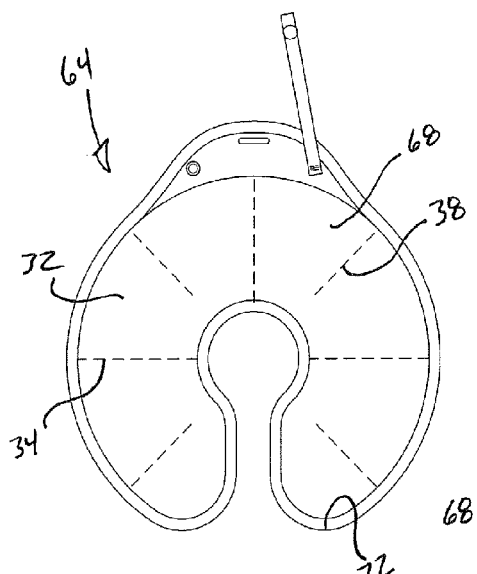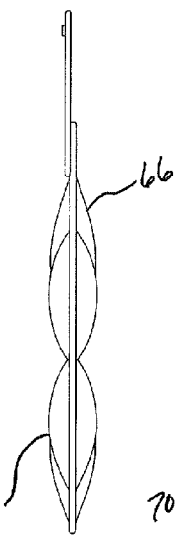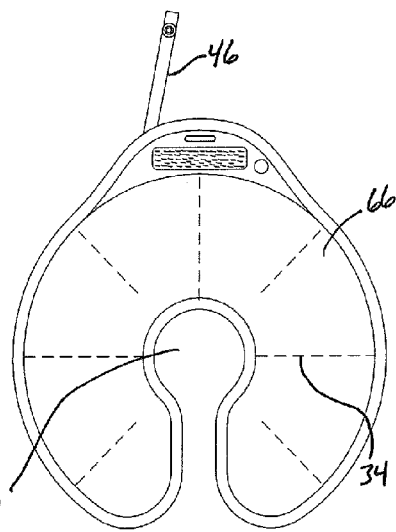
FIG. 31      FIG. 32      FIG. 33
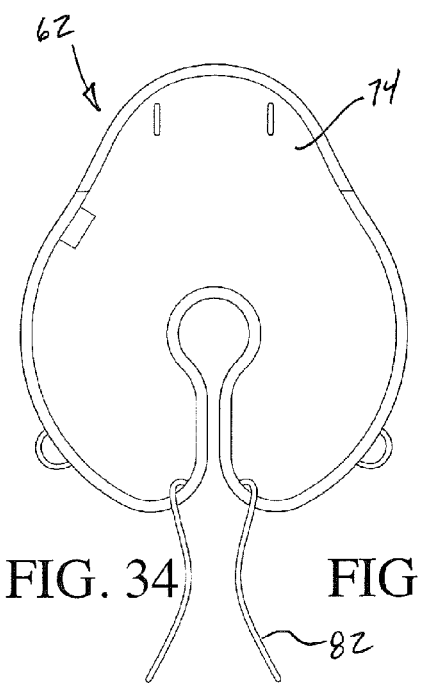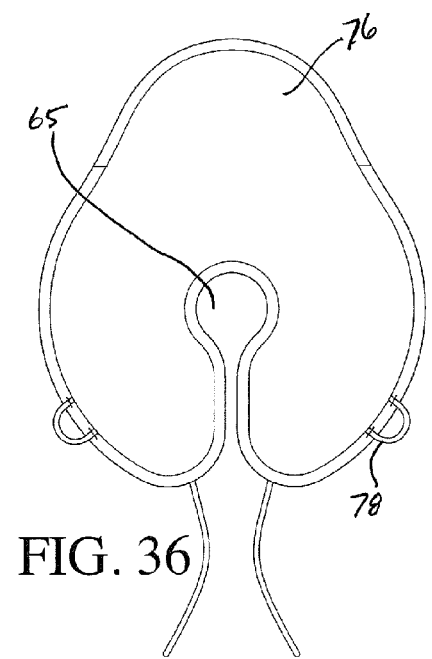
FIG. 34      FIG. 35      FIG. 36

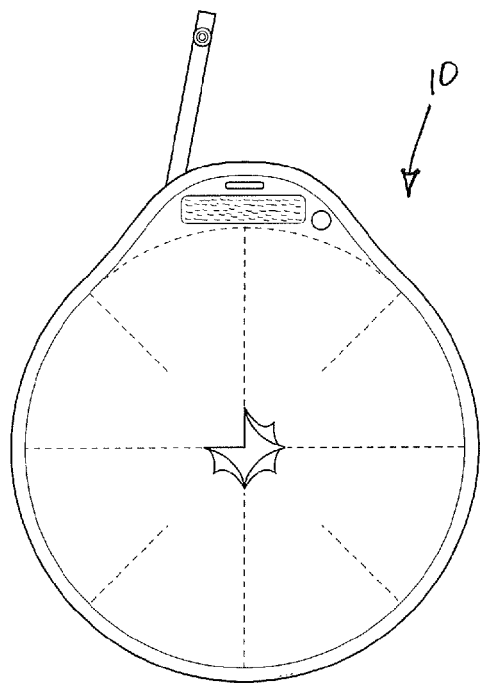 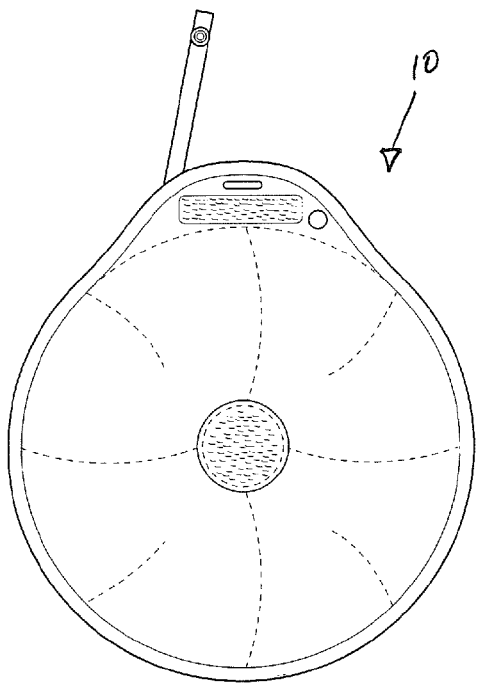
FIG. 43    FIG. 44
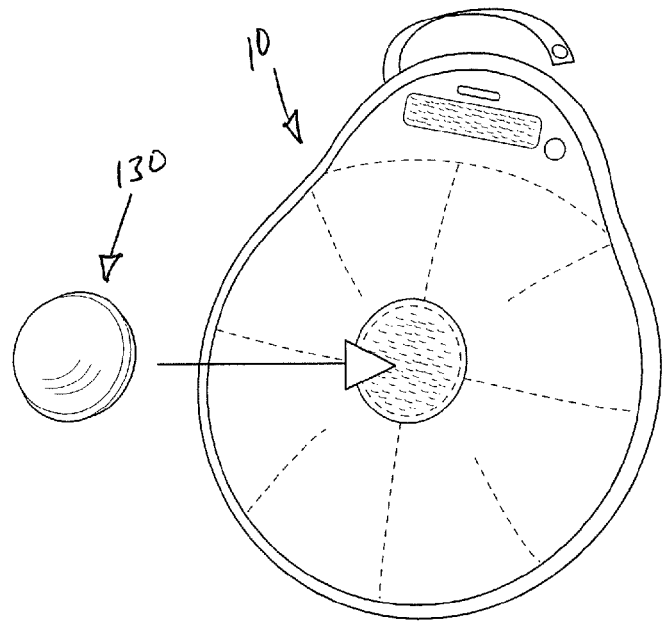 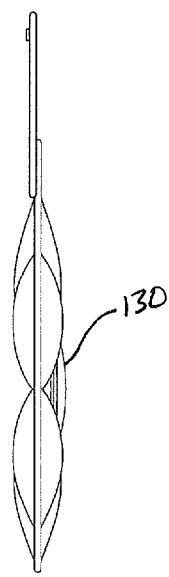
FIG. 45    FIG. 46

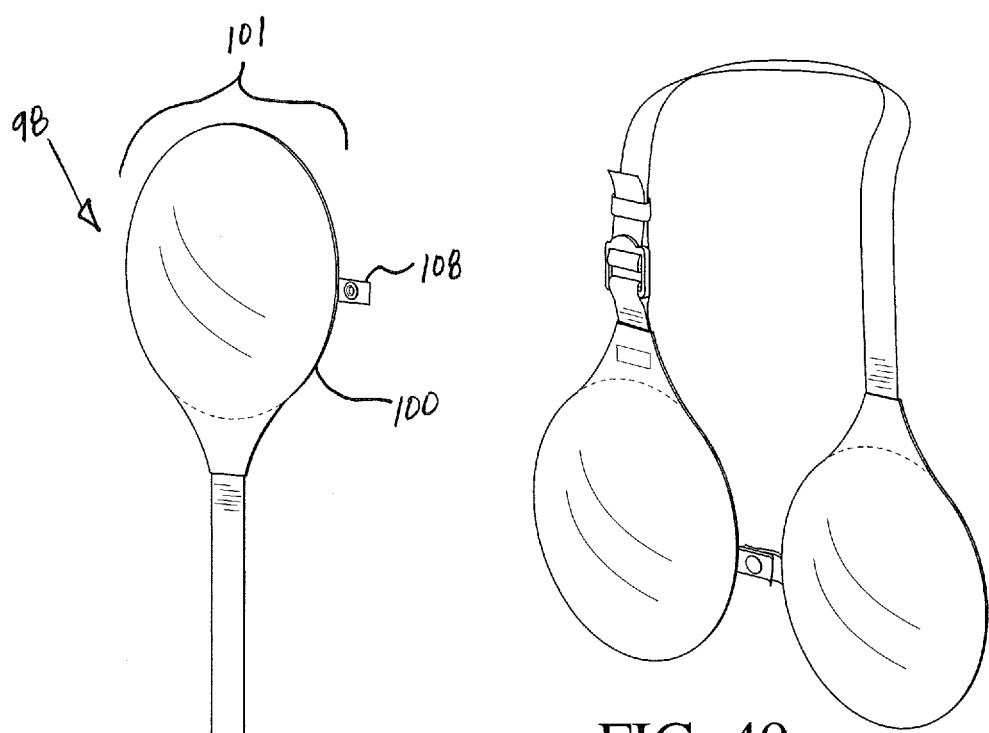
FIG. 49
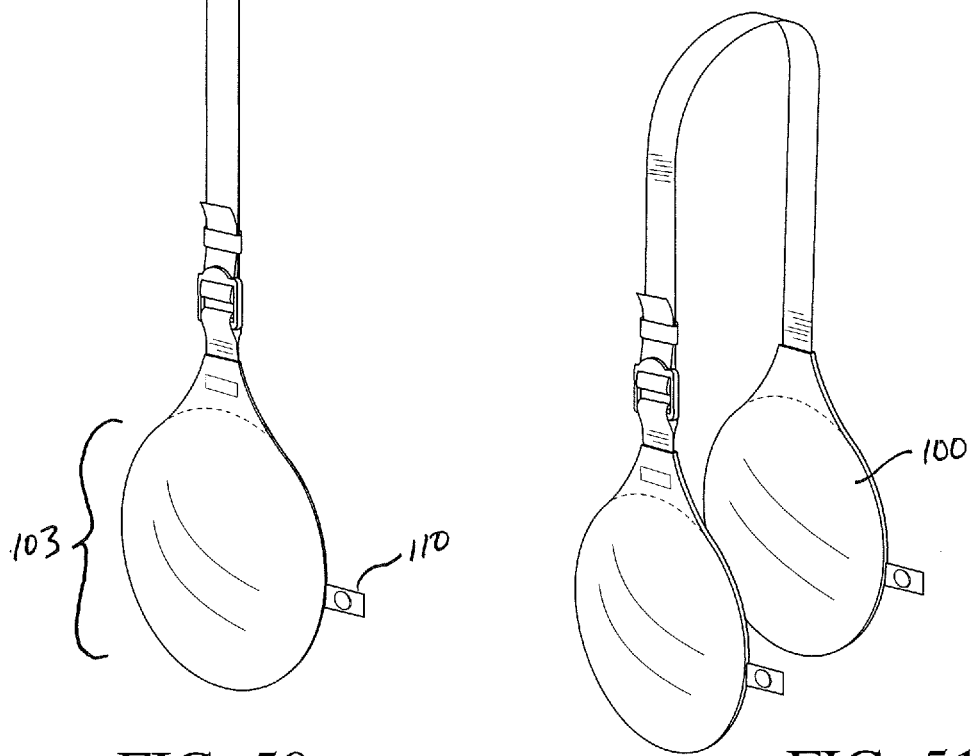
FIG. 50
FIG. 51

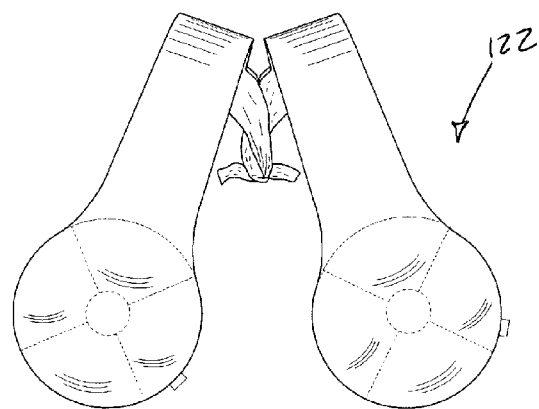
FIG. 64
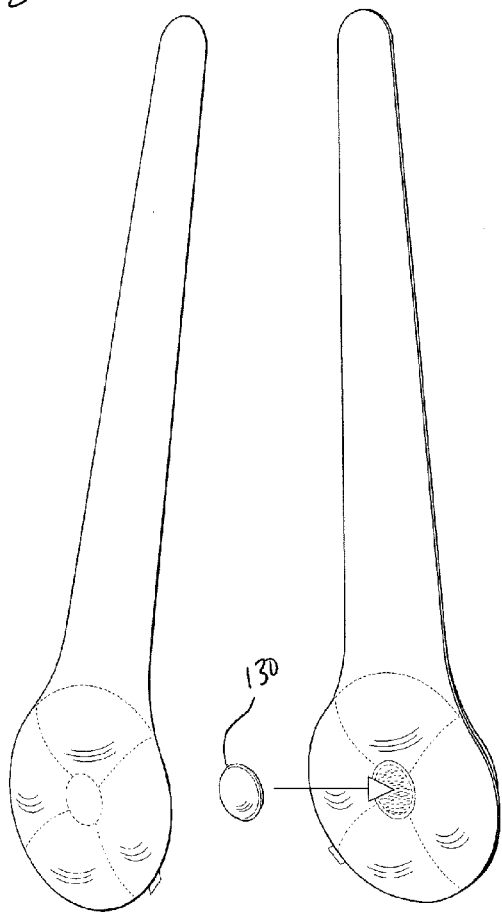
FIG. 65  FIG. 66
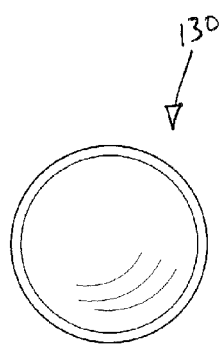  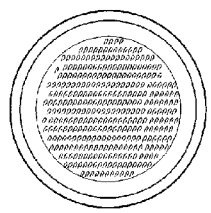
FIG. 67  FIG. 68  FIG. 69

LACTATION AID AND SOOTHING GARMENT

BACKGROUND OF THE INVENTION

While specifically addressing the complications that can arise during breast feeding, it should be noted that most women find the vast majority of their nursing experiences to be some of their most intimate and beautiful times with their children. Many mothers experience difficulties with lactation. Within 72 hours of giving birth, often women experience engorgement of their breasts as their breasts start producing more milk to meet the needs of a nursing infant. More blood flows to the breasts and some of the surrounding tissue can swell, eliciting swollen, tender, throbbing breasts. Fortunately, engorgement passes quickly (24 to 48 hours if nursing regularly) for most women. Unfortunately, when engorgement does not resolve, it can lead to more serious and painful complications of breastfeeding. This can result in problems not only for the mother but for the feeding infant as well.

Clogged ducts are the enemy of a nursing mother. Milk does not flow freely with clogged ducts, which can result in the feeding infant's nutritional demands not being met. Sometimes a milk duct leading from the milk-making cells through an area of the breast and nipple get plugged (blocked), resulting in a tender lump beneath the areola, and potentially a wedge-shaped area of redness extending from the lump back towards the wall of the chest. While the initial discomfort of a clogged duct may come and go, if left untreated clogged ducts may become infected resulting in mastitis or diminished milk supply.

Mastitis is an infection of the breast tissue. In addition to breast pain, swelling, warmth, and redness of the breast, mastitis also includes flu-like symptoms, such as headache, fever, chills, and exhaustion.

Recommended treatment of engorgement, clogged ducts, and mastitis include the application of heat or cold therapy as well as the continued expression of milk from the breast(s), either by nursing or pumping. By reducing the speed of impulses conducted by nerve fibers pain sensations are reduced by cold. Additionally, cold causes constriction of the blood vessels and veins thereby reducing swelling. While it is not well known how the administration of heat reduces pain, it is well known that heat therapy produces a "relaxing and soothing" feeling to the patient as well as opening blood vessels, increasing blood flow, and helping to increase milk flow. When a nursing mother is able to relax, the oxytocin hormone is released, which stimulates milk expulsion while stimulating prolactin, which helps in the production of milk.

New breast feeding mothers are prone to neck tension and discomfort from looking down at their babies and breasts while nursing. This posture creates neck, head and shoulder tension, which can restrict blood-flow in the neck area, which in turn may restrict blood flow to the breast area resulting in possible restricted milk production and restricted milk expulsion.

While often painful, emptying the milk from the affected breast frequently is important to recovering from the aforementioned conditions. In particular, pumping via an automated breast pump can be beneficial due the fact that the pumping speed and suction can be increased/decreased accordingly.

In order to provide some relief, individual cold packs and warm compresses are utilized. However, this approach is cumbersome and inefficient, requiring a "spare hand" to hold the pack or compress in place, that a nursing mother simply does not have. A mother simply cannot apply a compress, pump (or nurse), and care for her infant simultaneously with just two hands. When treating for clogged milk ducts, in addition to heat and suction, massaging the affected area becomes impossible. Existing products require a mother to stuff thermal packs inside her bra with direct contact with the skin, which can be uncomfortable, unsightly and can possibly burn the skin.

Beyond nursing mothers, this invention is also well suited for woman who experience breast discomfort from breast cancer treatments and any type of breast related surgery, hot flashes and even PMS. Nursing women and non-nursing women who suffer from Raynaud's Disease can also benefit greatly from this invention in that it aids in blood circulation to effected areas. Inflammation from treatments and surgery can be treated with cold breast therapy, and the combination of warm and cold therapy helps circulate good blood to the effected area resulting in faster recovery times.

SUMMARY OF THE INVENTION

At the heart of the present invention is a soothing garment and hands-free lactation aid that allows for the application of heat and cold therapy to both breasts and the neck. It is adjustable, can be worn over clothing, is modular for customization, is washable, and employs a natural, non-toxic, thermal medium that retains both warmth and cold for reasonably long periods of time. In an alternate embodiment the therapeutic garment supports a breast pump allowing the user to simultaneously pump while applying warm or cold therapy to her breasts, while having free hands to massage breasts, if trying to loosen clogged milk ducts.

In addition to applying soothing comfort to the breast and neck area the present invention is also suited to be worn around the waist to help ease discomfort from the pelvic and lower back areas with the application of heat and cold therapy.

BRIEF DESCRIPTION OF THE DRAWINGS

FIG. 8 is a top view of the first embodiment breast cozy;

FIG. 9 is a right-side view of the first embodiment breast cozy;

FIG. 10 is a bottom view of the first embodiment breast cozy;

FIG. 11 is a top view of the first embodiment cozy cover;

FIG. 12 is a right-side view of the first embodiment cozy cover;

FIG. 13 is a bottom view of the first embodiment cozy cover;

FIG. 14 is a top view of the second embodiment breast cozy;

FIG. 15 is a right-side view of the second embodiment breast cozy;

FIG. 16 is a bottom view of the second embodiment breast cozy;

FIG. 17 is a top view of the second embodiment cozy cover;

FIG. 18 is a right-side view of the second embodiment cozy cover;

FIG. 19 is a bottom view of the second embodiment cozy cover;

FIG. 24 is a partial top view illustrating the adjustable neckband secured within a first embodiment cozy cover;

FIG. 25 is a partial top view illustrating the adjustable neckband secured within a second embodiment cozy cover;

FIG. 31 is a top view of the third embodiment breast cozy;

FIG. 32 is a right-side view of the third embodiment breast cozy;

FIG. 33 is a bottom view of the third embodiment breast cozy;

FIG. 34 is a top view of the third embodiment cozy cover;

FIG. 35 is a right-side view of the third embodiment cozy cover;

FIG. 36 is a bottom view of the third embodiment cozy cover;

FIG. 43 is a top view of a first embodiment breast cozy showing a center fill hole area before being filled;

FIG. 44 is a top view of a first embodiment breast cozy with a central circular loop fastener stitched down to secure the thermal media in place and allow for the attachment of a thermal nipple soother;

FIG. 45 is a perspective view of a first embodiment breast cozy with a thermal nipple soother being attached to the central circular loop fastener;

FIG. 46 is a right-side view of a first embodiment breast cozy with a thermal nipple soother attached;

FIG. 49 is a perspective view of a second embodiment lactation aid and soothing garment wherein the breast cozies are connected via a fastener;

FIG. 50 is a perspective view of a second embodiment lactation aid and soothing garment;

FIG. 51 is a perspective view of a second embodiment lactation aid and soothing garment folded about its midpoint;

FIG. 64 is a front view of a fourth embodiment lactation aid and soothing garment tied to a second fourth embodiment lactation aid and soothing garment FIG. 65 is a front perspective view of the fourth embodiment lactation aid and soothing garment;

FIG. 66 is a back perspective view of the fourth embodiment lactation aid and soothing garment with a thermal nipple soother being attached;

FIG. 67 is a top view of the thermal nipple soother;

FIG. 68 is a right-side view of the thermal nipple soother; and

FIG. 69 is the back view of the thermal nipple soother.

DETAILED DESCRIPTION

Figure 1:
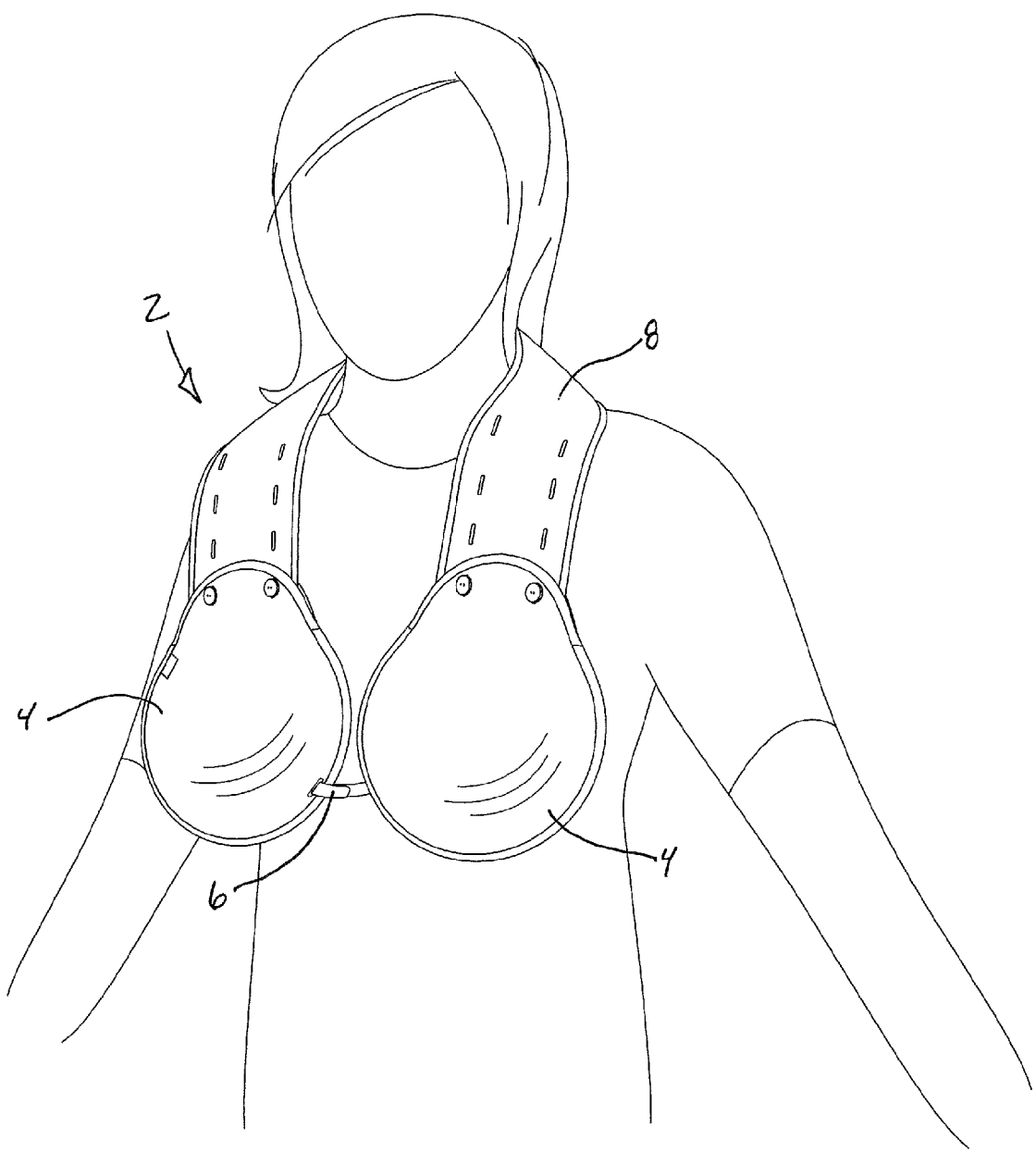
FIG. 1 is a perspective view of a first embodiment lactation aid and soothing garment shown in use.
Figures 2, 3, 4:
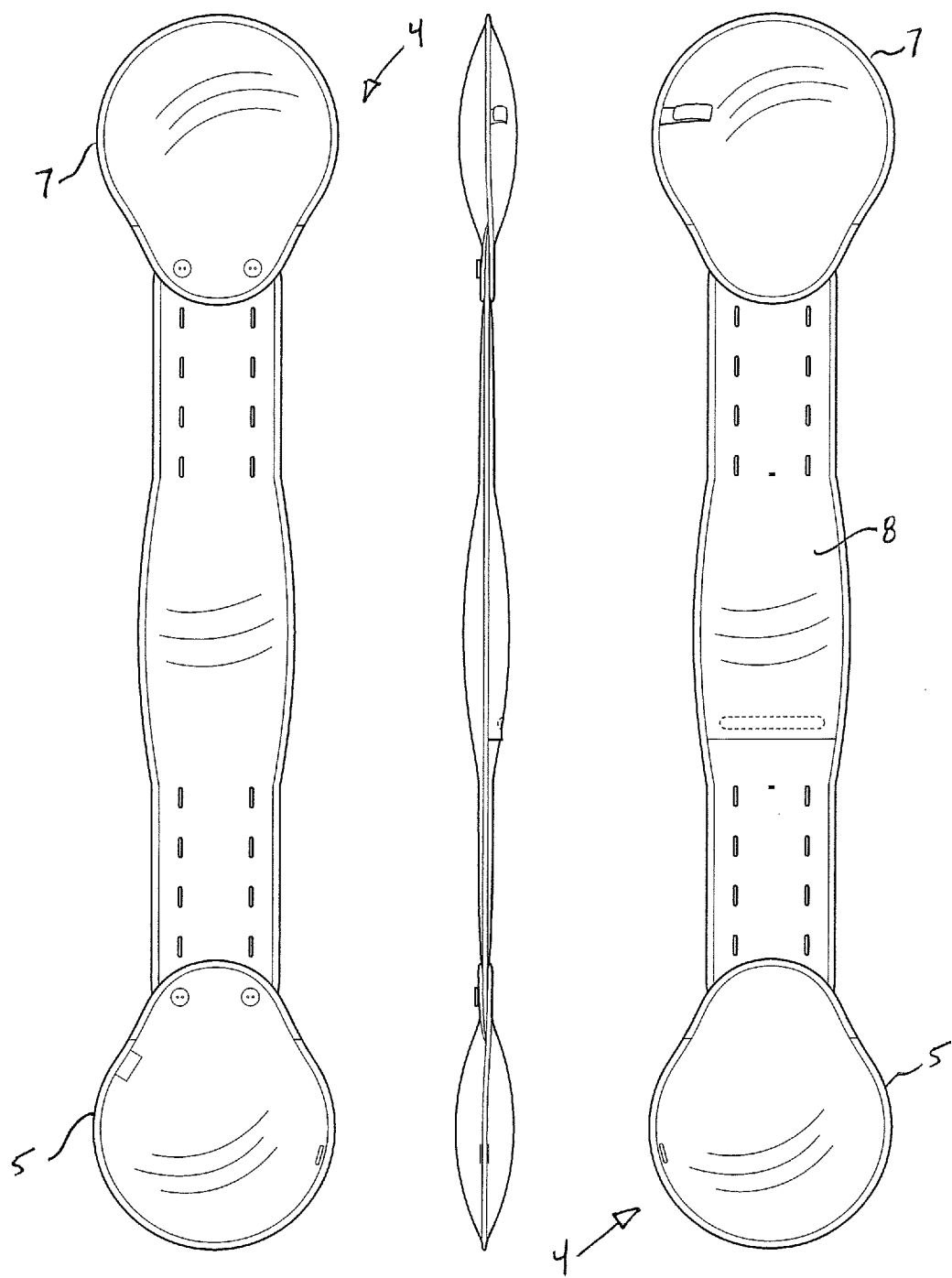
FIG. 2 is a top view of a first embodiment of the lactation aid and soothing garment.
FIG. 3 is a right-side view of a first embodiment of the lactation aid and soothing garment.
FIG. 4 is a bottom view of a first embodiment of the lactation aid and soothing garment.

FIG. 1 is a perspective view of a first embodiment lactation aid and soothing garment 2 shown in use. Visible from the outside, garment 2 has two first embodiment cozy covers 4, a pairing strap 6 that connects cozy covers 4, and an adjustable neckband 8. FIGS. 2-4 are simply top, right-side, and bottom views of first embodiment lactation aid and soothing garment 2 with first embodiment cozy cover 4, respectively. It can be seen on FIG. 2-4 that cozy covers 4 are bulbous due to fact that they contain first embodiment breast cozies 10, illustrated in FIG. 5.

Figure 5:
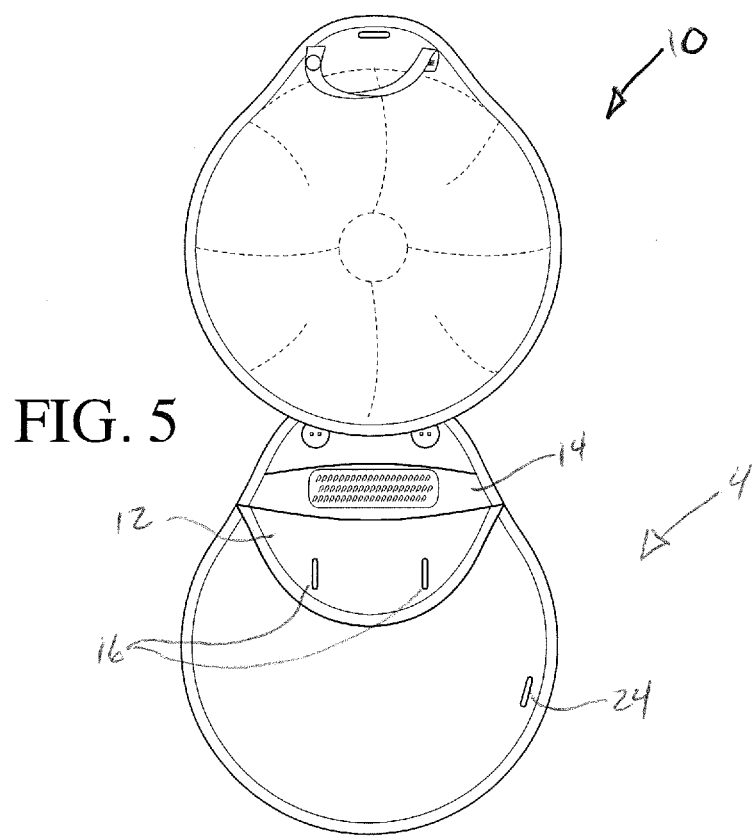
FIG. 5 is a top view illustrating how a first embodiment breast cozy is inserted into a first embodiment cozy cover.

Looking at FIG. 5, details of cozy cover 4 are visible. Cozy cover 4 is generally a circular or egg-shaped sealable pocket adapted for the insertion and retention of breast cozy 10. Cozy cover 4 is formed from two substantially similar egg-shaped halves, an outer fabric half 12 and an inner fabric half 14 stitched about a portion of their exterior perimeter to form a openable, sealable pocket capable of retaining breast cozy 10.

Figure 48:
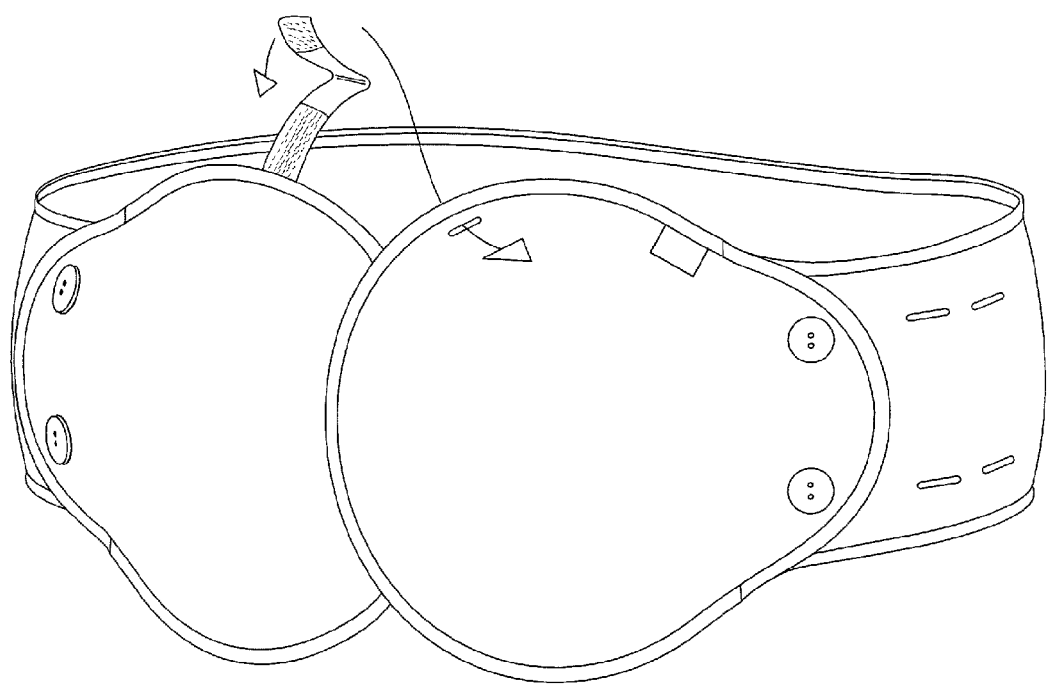
FIG. 48 is a perspective view illustrating how to arrange the first embodiment of the lactation aid and soothing garment into the alternate method of use illustrated in FIG. 47.
Figures 52, 53, 54:
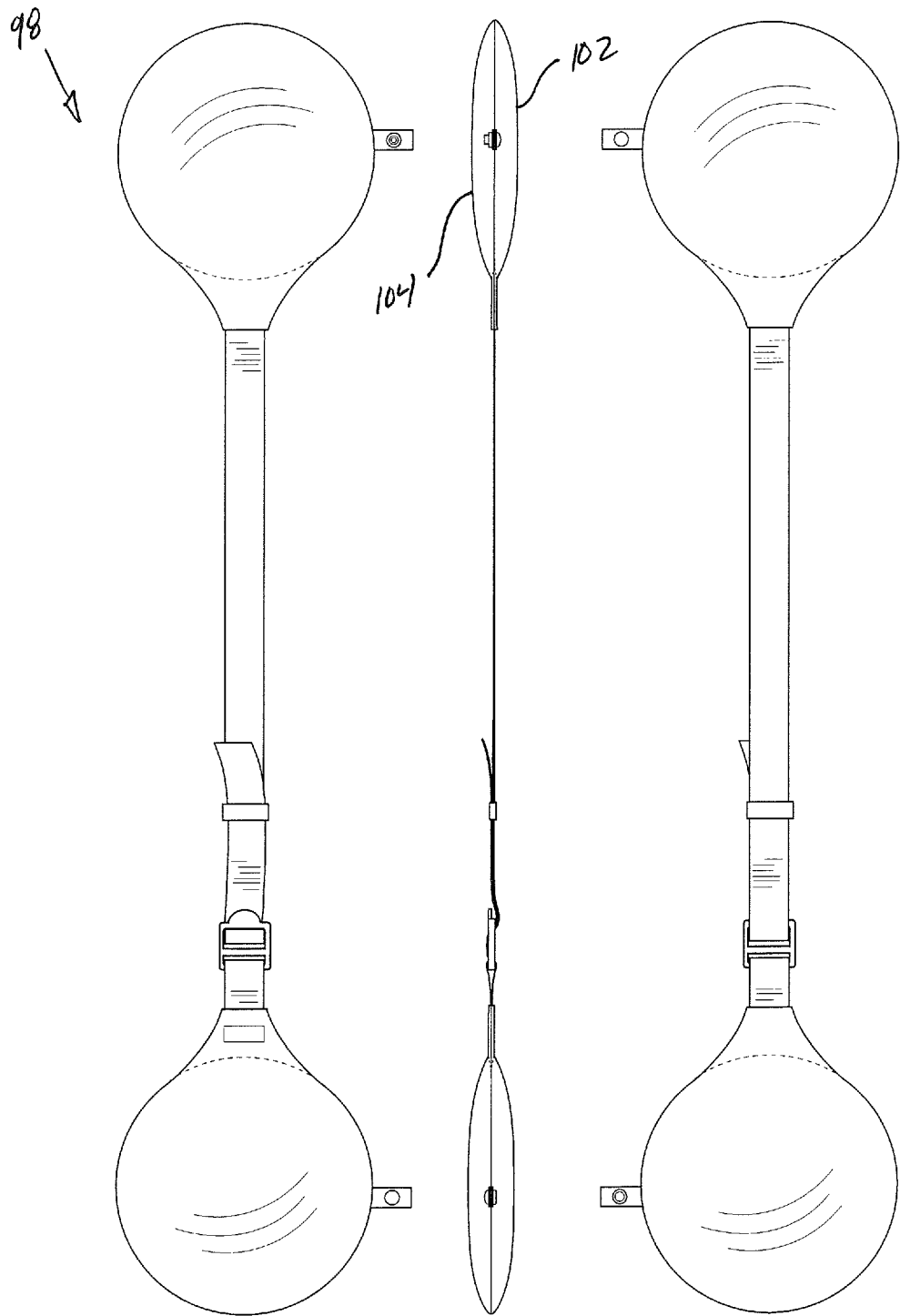
FIG. 52 is a top view of a second embodiment lactation aid and soothing garment.
FIG. 53 is a right-side view of a second embodiment lactation aid and soothing garment.
FIG. 54 is a bottom view of a second embodiment lactation aid and soothing garment.
Figure 55:
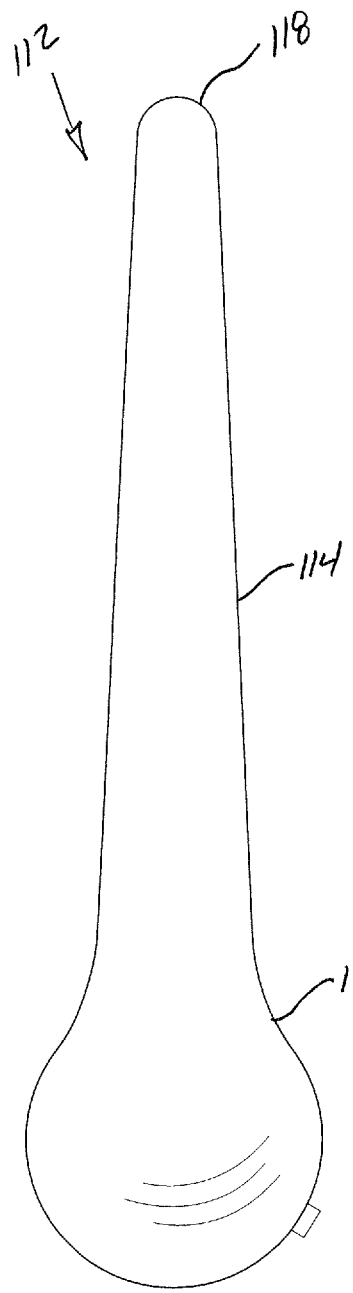
FIG. 55 is a top view of a third embodiment lactation aid and soothing garment.
Figure 56:
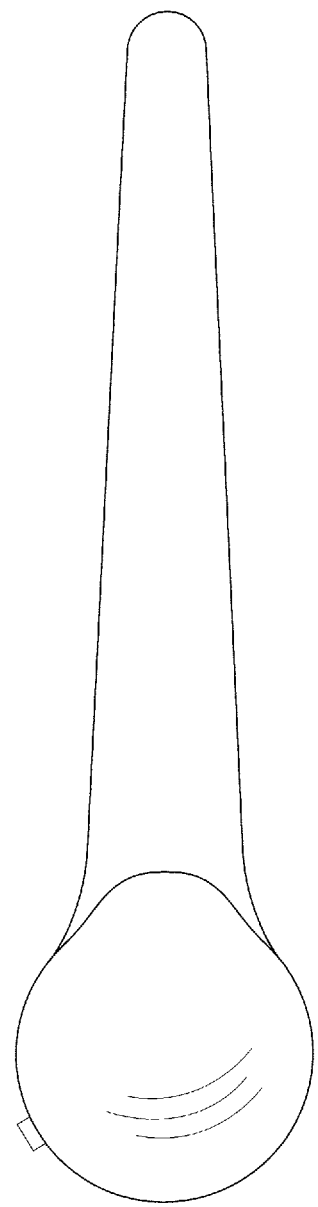
FIG. 56 is a back view of a third embodiment lactation aid and soothing garment.
Figure 57:
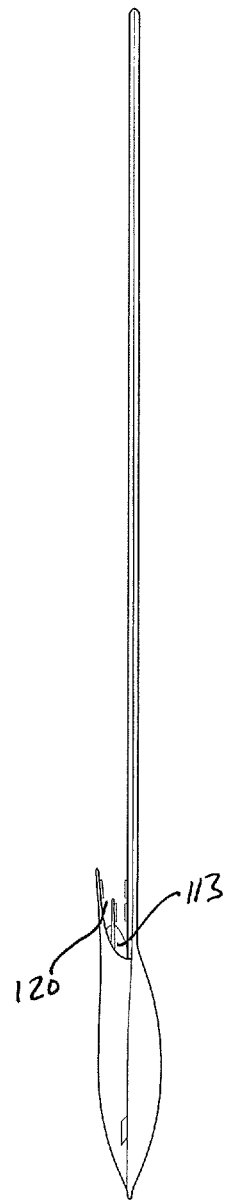
FIG. 57 is a right-side view of a third embodiment lactation aid and soothing garment.

The stitching that joins the fabric halves 12, 14, terminates at the upper section (a lobe portion) of the cozy cover 4 as to form an openable flap 15 for the insertion of breast cozy 10. Outer fabric half 12 has two apertures 16 formed therethrough for receipt of a garment fasteners 18 affixed to said inner fabric half 14. As illustrated garment fasters 18 are buttons; however, it should be noted that any garment fastener or mechanical fastener such as a tie, dome fastener, or hook-and-loop fastener may be used. A one-half mating strip of a hook-and-loop fastener 20 is affixed below garment fasters 18 on inner fabric half 14 for sealing engagement with a counterpart one-half mating strip 22 located on breast cozy 10 as illustrated in FIG. 10. Pairing aperture 24 extends through cozy cover 4 and resides along the side perimeter of cozy cover 4. Pairing aperture is configured to receive pairing strap 6. As visible in FIGS. 3-4 pairing strap 6 can be stitchedly affixed at its proximate end about the perimeter of cozy cover 4 with a free distal end for passage through pairing aperture 24. As is illustrated in FIG. 48, pairing strap 6 employs both hooks and loops of a hook-and-loop fastener about one face so as to allow pairing strap 6 to fasten to itself after passage through pairing aperture 24. As is illustrated in FIGS. 3 and 4 pairing aperture 24 resides therethrough a first cozy cover 5, while pairing strap 6 is stitchedly affixed to second cozy cover 7. It should be noted that any garment fastener or mechanical fastener such as a tie, dome fastener, or hook-and-loop fastener may be used. Additionally, pairing strap 6 could be a separate item that is not stitchedly affixed to a cozy cover. In this scenario a pairing aperture would pass therethrough both first cozy cover and second cozy cover. To secure first cozy cover to second cozy cover, pairing strap 6 would simply be placed through both pairing apertures and then fastened to itself.

While cozy covers 4 can be made from any fabric, easy to care for fabrics, such as 100% natural cotton and synthetic polyester, or a combination of both, are ideal choices, for comfort, durability, and being machine washable.

Figure 6:
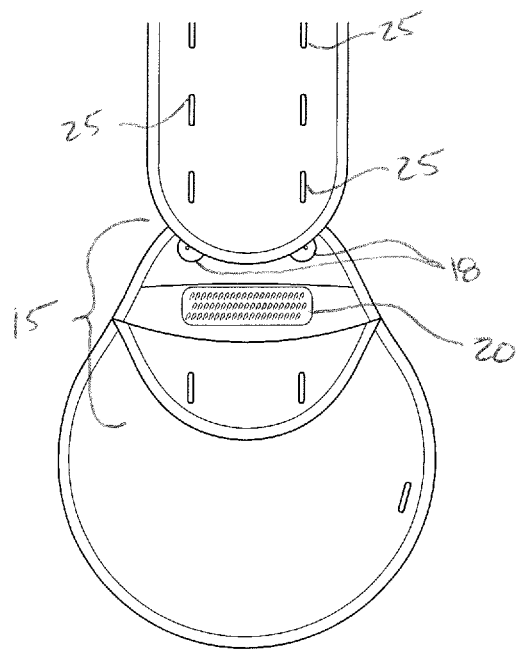
FIG. 6 is a partial top view illustrating how the adjustable neckband is inserted into a first embodiment cozy cover wherein a section of the cozy cover has been folded downward to reveal the interior of the cozy cover.
Figure 7:
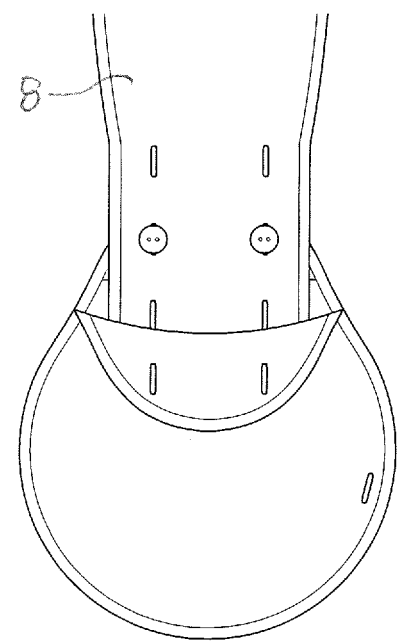
FIG. 7 is a partial top view illustrating the adjustable neckband secured within a first embodiment cozy cover, wherein a section of the cozy cover has been folded downward to reveal the interior of the cozy cover.
Figure 37:
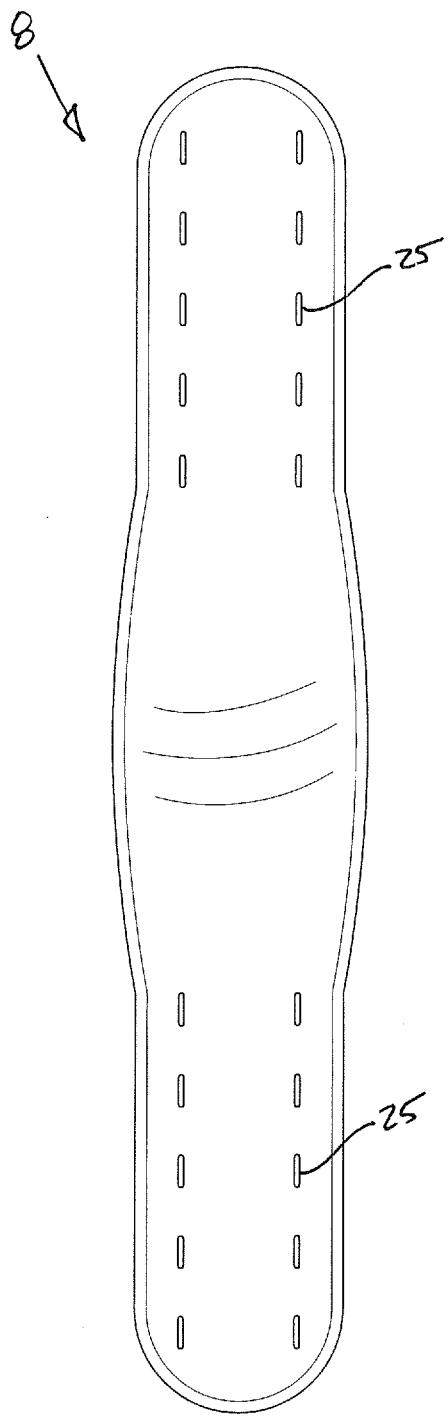
FIG. 37 is a top view of the adjustable neckband.
Figure 38:
FIG. 38 is a right-side view of the adjustable neckband.
Figure 39:
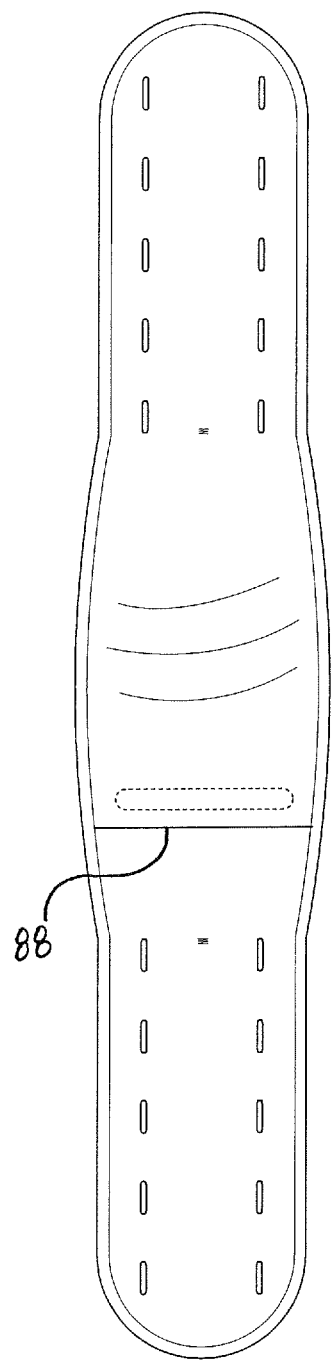
FIG. 39 is a bottom view of the adjustable neckband.
Figure 40:
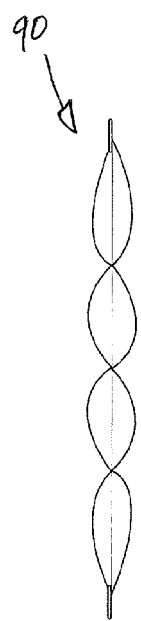
FIG. 40 is a right-side view of the therapeutic neckband insert.
Figure 41:
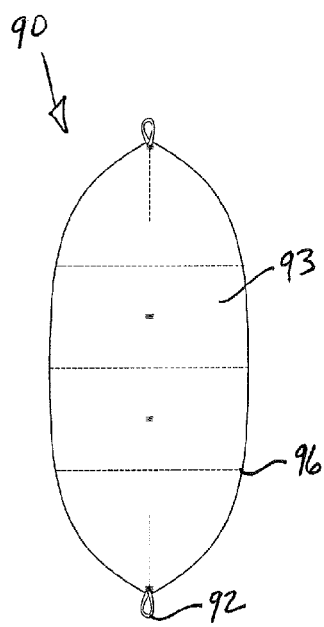
FIG. 41 is a top view of the therapeutic neckband insert.

The neckband 8 is formed from two substantially similar shaped fabric strips that are stitched together, around their perimeter, to form a unitary neckband. As is illustrated in FIGS. 6-7 adjustable neckband 8 can extend into, and be retained within cozy cover 4 via garment fasteners 18 operating in concert with neckband apertures 25 and apertures 16, accounting for the adjustable length of neckband 8. Designed to accommodate a variety of body types, neckband 8 is designed to never be too short, nor fit too snuggly around the user's neck/shoulders, and as such prevents chaffing. Neckband apertures 25 reside in pairs and in parallel configuration at both ends of neckband 8 as is illustrated in FIGS. 37-39. The user simply selects their preferred length, places garment fasteners 18 through neckband apertures 25 and then finally secures cozy cover 4 to neckband 8 by then placing fasteners 18 through apertures 16 located on outer fabric half 12. To maximize heat/cold retention, the user will tuck the extra length of the neckband 8 into the cozy cover 4 on the top surface of the breast cozy 10, so as to not hinder the transfer of heat/cold from the thermal mass to the breast. The extra length of the neckband 18 will serve as an insulator, helping to drive the heat/cold towards the breast. The ends of the neckband 8 may contain a reflective insulating material (not shown) housed between the substantially similar fabric strips at each end of the neckband 8, or it may also be affixed to the inner face of the neckband 8 in the same region. Additionally the interior face of outer fabric half 12 may also have a reflective insulating material (not shown) to drive the heat/cold towards the breast.

While neckband 8 can be made from any fabric, easy to care for fabrics, such as 100% natural cotton and synthetic polyester, or a combination of both, are ideal choices, for comfort, durability, and being machine washable.

Figure 42:
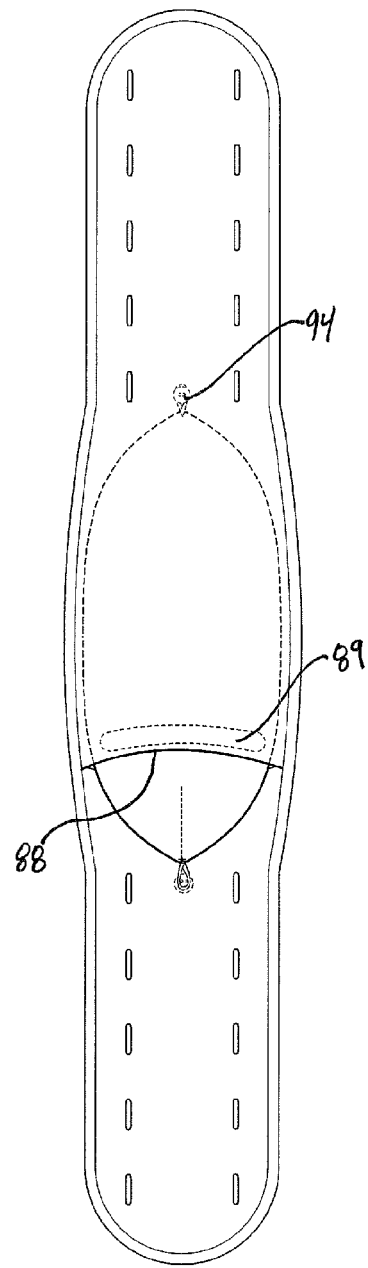
FIG. 42 is a bottom partial-phantom view of the adjustable neckband with a partially inserted therapeutic neckband insert.

For additional thermal therapy, neckband 8 includes a pocket 88 for insertion of a thermal mass insert 90, illustrated in FIG. 37-42. Thermal mass insert 90 is an oblong shaped fabric container that can be filled with any suitable thermal mass that can be placed both in the freezer and microwave, such as natural grains with herbal scents, thermal beads, gel packs, gel beads, or clay. Thermal mass insert 90 has two retention loops 92 located at opposite ends allowing insert 90 to be secured within pocket 88 via buttons 94 stitched within pocket 88. Thermal mass insert 90 has four distinct compartments 93 for retaining the thermal mass. Compartments 93 are separated by stitch lines 96 that allow thermal mass insert to conform to the user's neck/upper shoulder region by bending along the stitch lines 96, providing pain relief to an area often fatigued by nursing. Stitch lines 96 also serve to more evenly distribute the thermal mass throughout insert 90. Thermal mass insert 90 can be constructed from any suitable or desired fabric, and while illustrated with buttons securing insert 90 within neckband pocket 88, any suitable fastening means could be employed such as a tie, dome fastener, or hook-and-loop fastener. For additional retention, a strip of hook-and-loop fastener 89 can be placed within pocket 88 as illustrated in FIG. 42 for mating retention with a strip of hook-and-loop fastener.

Turning now to FIGS. 8-10 first embodiment breast cozy 10 is visible. Breast cozy 10 is also configured in a circle or egg-shape, and has an inner concave face 26 and an outer concave face 28 as can be seen in FIG. 9, the right-side view. Central circular stitched region 30 is empty as to not apply direct warmth to the nipple, which is ideal for the general population; however, for women with Raynaud's Disease, direct warmth to the nipple is recommended. For this scenario of desired heat on the nipple and also for those with chapped and sore nipples who need cold on their nipples, a central thermal nipple soother 130 can be separately heated or cooled and attached in the center of the cozy (See FIGS. 45 and 66-69), via a circular one-half mating strip of hook-and-loop fastener affixed to central circular stitched region 30. This allows for simultaneous hot or cold therapy on the breast; warm breast with cold nipples, cold breast with warm nipples or full coverage warm or full coverage cold. Nipple soother 130 is simply a small fabric or polymer disk containing a thermal mass that is capable of being placed in a freezer for cooling or in a microwave for warming. Nipple soother 130 has one-half of a hook-and-loop fastener attached about one face as illustrated in FIGS. 68 and 69 for mating attachment with breast cozy 10 and 50 or with fourth embodiment lactation aid and soothing garment 122, illustrated in FIG. 66.

Thermal mass holding compartments 32 radiating out 360° about a perimeter of said central circular stitched region 30. Thermal mass holding compartments 32 are defined by stitch lines 34 extending normally from said perimeter of said central stitched region 30 to a stitched circle 36 about the perimeter of said cozy 10, and keep the thermal mass evenly distributed throughout cozy 10. As illustrated in FIGS. 8-9 four thermal mass holding compartments 32 are illustrated. To aid in obtaining a cupped, form fitting design, form-fitting stitch lines 38 extend normally from stitched circle 36 partially bisecting thermal mass holding compartments 32. Form-fitting stitch lines 38 allow thermal mass holding compartments 32 to bend along lines 38 in addition to bending along stitch lines 34, since no thermal mass/media resides along form-fitting stitch lines 38.

A hanging aperture 40 is formed therethrough a top edge of cozy 10. The mating one-half strip of a hook-and-loop fastener 22 is affixed adjacent said aperture for mating engagement with one-half mating strip of a hook-and-loop fastener 20 on inner fabric half 14 of cozy cover 4. Again, any suitable fastening means could be employed such as a tie, dome fastener, or hook-and-loop fastener without departing from the scope of the invention. A first fastening means 44 is affixed adjacent said hook-and-loop fastener 22. As illustrated in FIG. 10 first fastening means 44 is the socket portion of a dome fastener, as is well known in the art. A fastening strap 46 having a proximate end affixed to a top edge of said cozy 10 on said outer concave face 28 and a second fastening means 48 adapted for mating engagement with said first fastening means 44 affixed to a distal end of said fastening strap 46. As illustrated second fastening means 48 is the dome of a dome fastener. FIGS. 11-13 illustrate first embodiment cozy cover 4 with first embodiment breast cozy 4 secured within.

Thermal mass compartments 32 are filled with any suitable thermal mass that can be placed both in the freezer and microwave, such as natural grains with herbal scents or non-toxic thermal beads, gel packs, gel beads, or clay. Second embodiment breast cozy 50 is illustrated in FIGS. 14-16. Breast cozy 50 is designed for larger breasts than first embodiment breast cozy 10. Second embodiment breast cozy 50 varies from cozy 10 in design of the thermal mass storage compartments 32. In order to obtain a contoured, form fit around a larger breasts, wedge shaped thermal mass voids 52 are created. Additionally, pleats 54 are employed to further aid in forming a large concave cup around the breast, allowing for maximum contact and comfort of the thermal medium with the breast. Pinching together and stitching (bar tacking) thermal mass voids 52 will create a pleat 54.

FIGS. 17-19 illustrate second embodiment cozy cover 56 with second embodiment breast cozy 50 secured within. Second embodiment cozy 56 only varies in construction from first embodiment cozy cover 4 by size and the addition of darts 58. Darts 58 are folds sewn into the fabric to help provide a three-dimensional shape to a garment to allow the second embodiment cozy cover 56 to conform to the shape of the breast. See FIGS. 24-25. The pleats 54 on breast cozy 50 correspond with the darts 58 on the cozy cover for optimum fit, conformability, comfort and performance.

FIGS. 43-44 illustrate how first embodiment breast cozy 10 is filled with the thermal mass/media. A central circular region is left open for filling. Once filled, the central region is stitched closed using a central circle fabric piece constructed of loop-fastener allowing for attachment of hook-fastener (or vice versa). Although first embodiment breast cozy 10 is illustrated, the central-fill method and applicable thermal nipper soother 130 is also applicable to second embodiment breast cozy 50.

Figure 20:
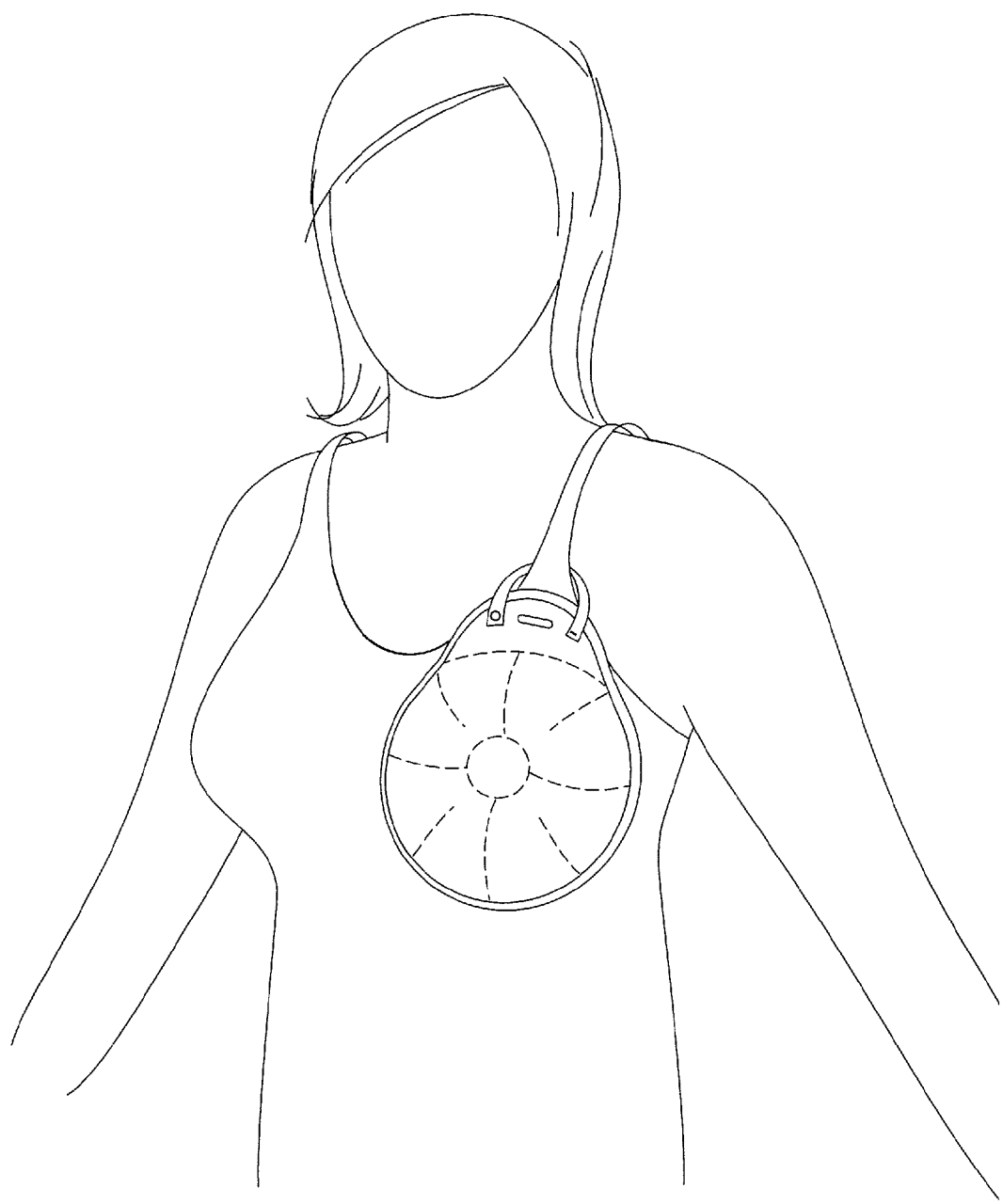
FIG. 20 is a perspective view of the first embodiment breast cozy shown in use with a camisole.
Figure 21:
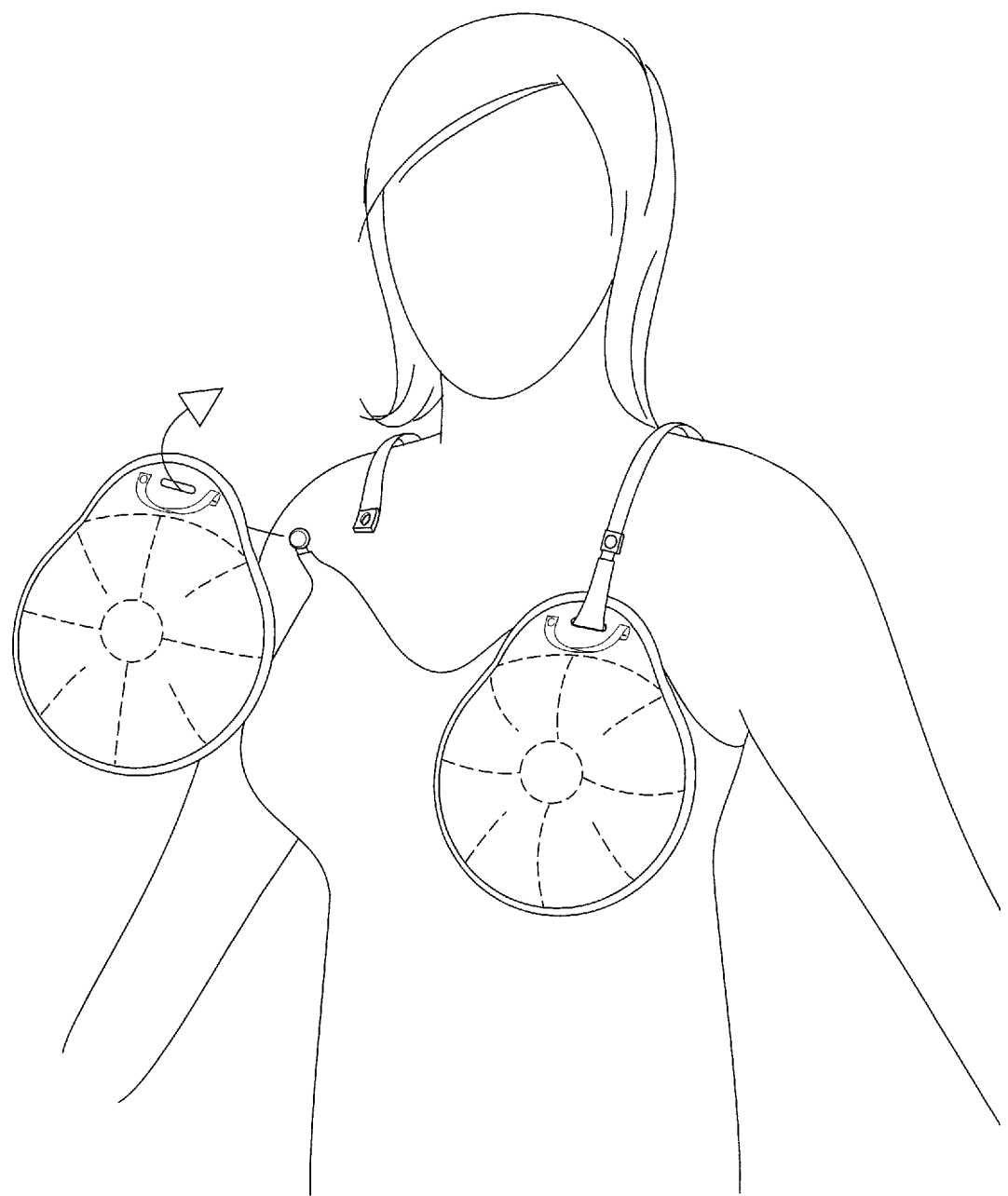
FIG. 21 is a perspective view of a first embodiment breast cozy shown in alternate method of use with a nursing camisole.
Figure 22:
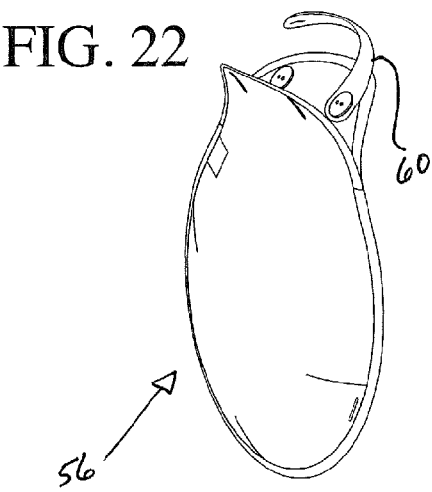
FIG. 22 is a perspective view of a second embodiment cozy cover with a connection strap partially attached.
Figure 23:
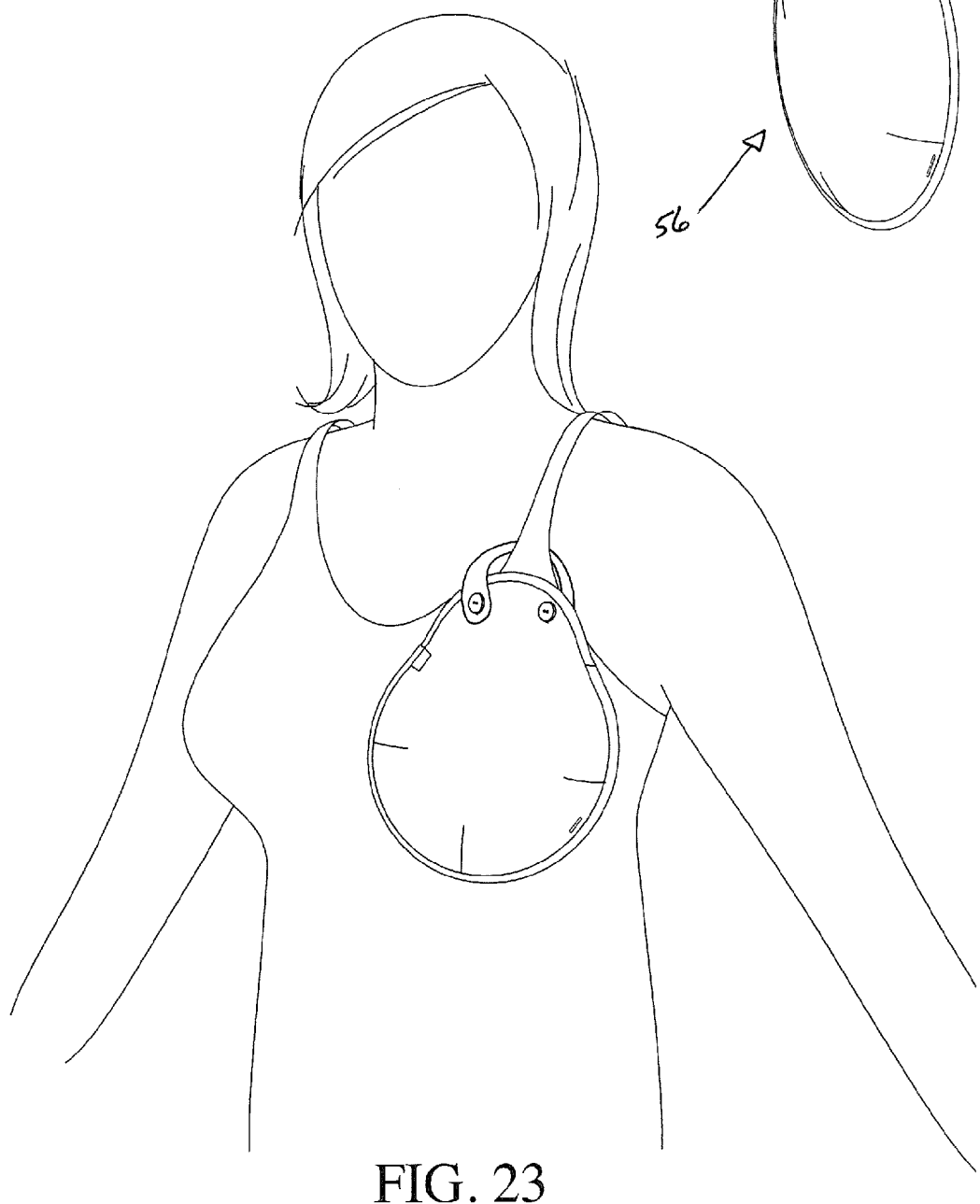
FIG. 23 is a perspective view of a second embodiment cozy cover attached to a camisole via a connection strap.
Figure 26:
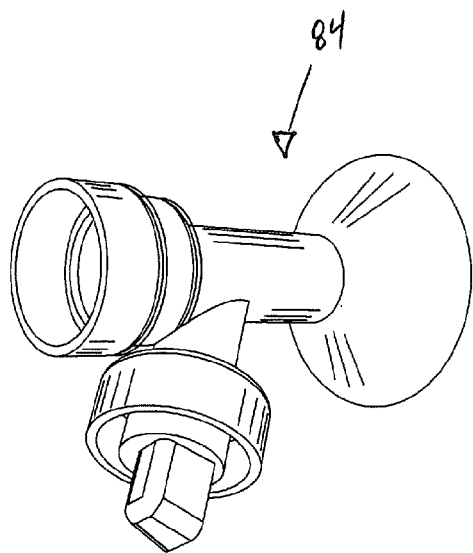
FIG. 26 is a perspective view of a breast pump flange.
Figure 27:
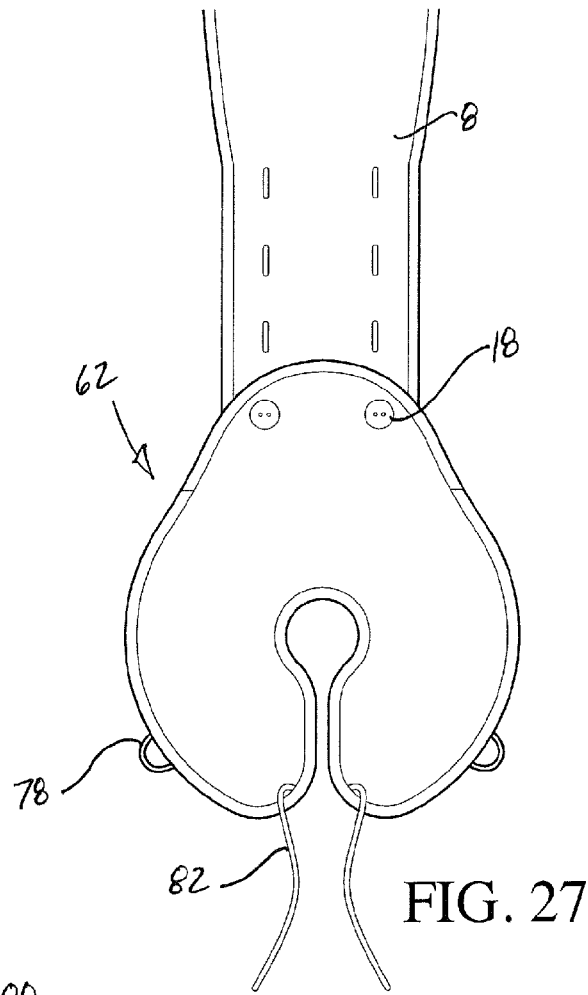
FIG. 27 is a partial top view illustrating the adjustable neckband secured within a third embodiment breast cozy.
Figure 28:
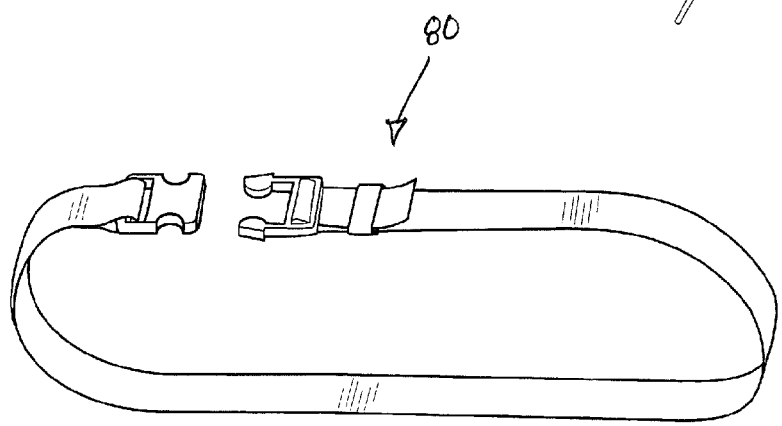
FIG. 28 is perspective view of the body belt.

FIG. 20 illustrates how first embodiment breast cozy 10 can be worn independently. A woman simply secures cozy 10 to her tank top, bra, or camisole via fastening strap 46 as illustrated. While FIG. 20 only illustrates first embodiment breast cozy 10, second embodiment breast cozy 50 can be used in an identical fashion. FIG. 21 shows and alternate method of use, wherein first embodiment breast cozy 10 (or second embodiment breast cozy 50) can be attached or hooked to a nursing camisole or nursing bra via hanging aperture 40. Breast cozy 10 or second embodiment breast cozy 50 can also be attached to a tank top, camisole, or nursing camisole, by first placing it within cozy cover 4 (or second embodiment cozy cover 56, when using second embodiment breast cozy 50) as illustrated in FIG. 23, via connection strap 60.

Figure 47:
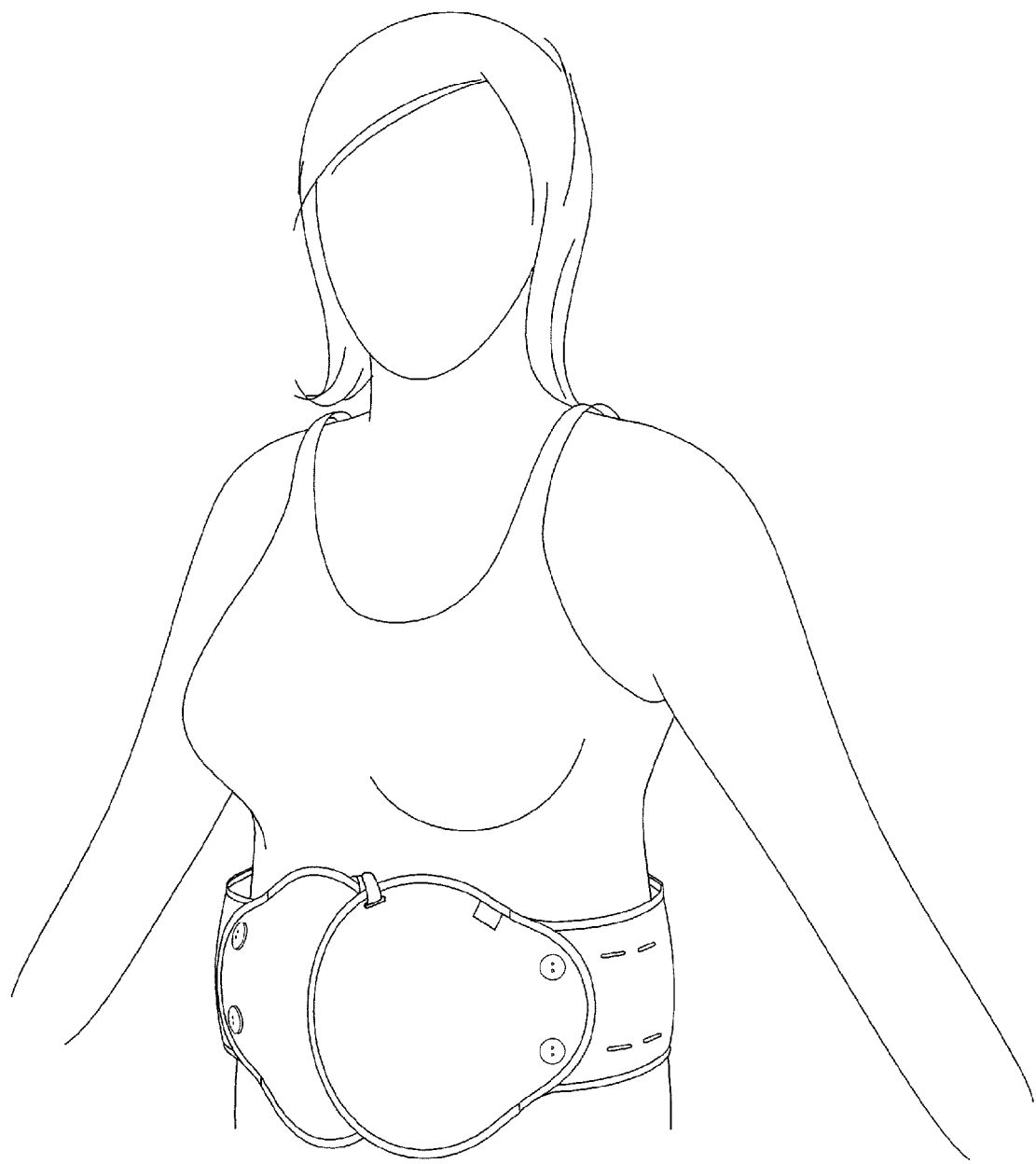
FIG. 47 is a perspective view of a first embodiment of the lactation aid and soothing garment shown in an alternate method of use.

First embodiment lactation aid and soothing garment 2 can also be used to sooth the pain and discomfort on other areas of the body associated with menstrual cramps, back pain or even an upset stomach, as is illustrated in FIG. 47-48.

Turning to FIGS. 26-30, third embodiment cozy cover 62 and breast cozy 64 are designed to accommodate a breast pump flange, as to allow a woman to wear the lactation aid and soothing garment 2 while breast pumping. Third embodiment breast cozy 64 is configured in a non-contiguous donut shape having an inner concave face 66 and an outer concave face 68, with a keyhole shaped void 70 extending from its center to an outer peripheral edge 72. A series of thermal mass holding compartments 32 are formed between the keyhole shaped void 70 and outer peripheral edge 72. The keyhole shaped void 70 is sized to accept the breast pump flange 84 and still provide the greatest amount of thermal therapy to the breast. Again, thermal mass holding compartments 32 are defined by stitch lines 34 extending normally from a perimeter of the keyhole shaped void to peripheral edge 72. As illustrated in FIGS. 31-33 four thermal mass holding compartments 32 are illustrated. To aid in obtaining a cupped, form fitting design, form-fitting stitch lines 38 extend normally from peripheral edge 72 partially bisecting thermal mass holding compartments 32. Form-fitting stitch lines 38 allow thermal mass holding compartments 32 to bend along lines 38 in addition to bending along lines 34, since no thermal mass resides along form-fitting stitch lines 38. All attachment means and fasteners are identical on third embodiment breast cozy 64 as first embodiment cozy 10 and second embodiment cozy 50.

Figure 29:
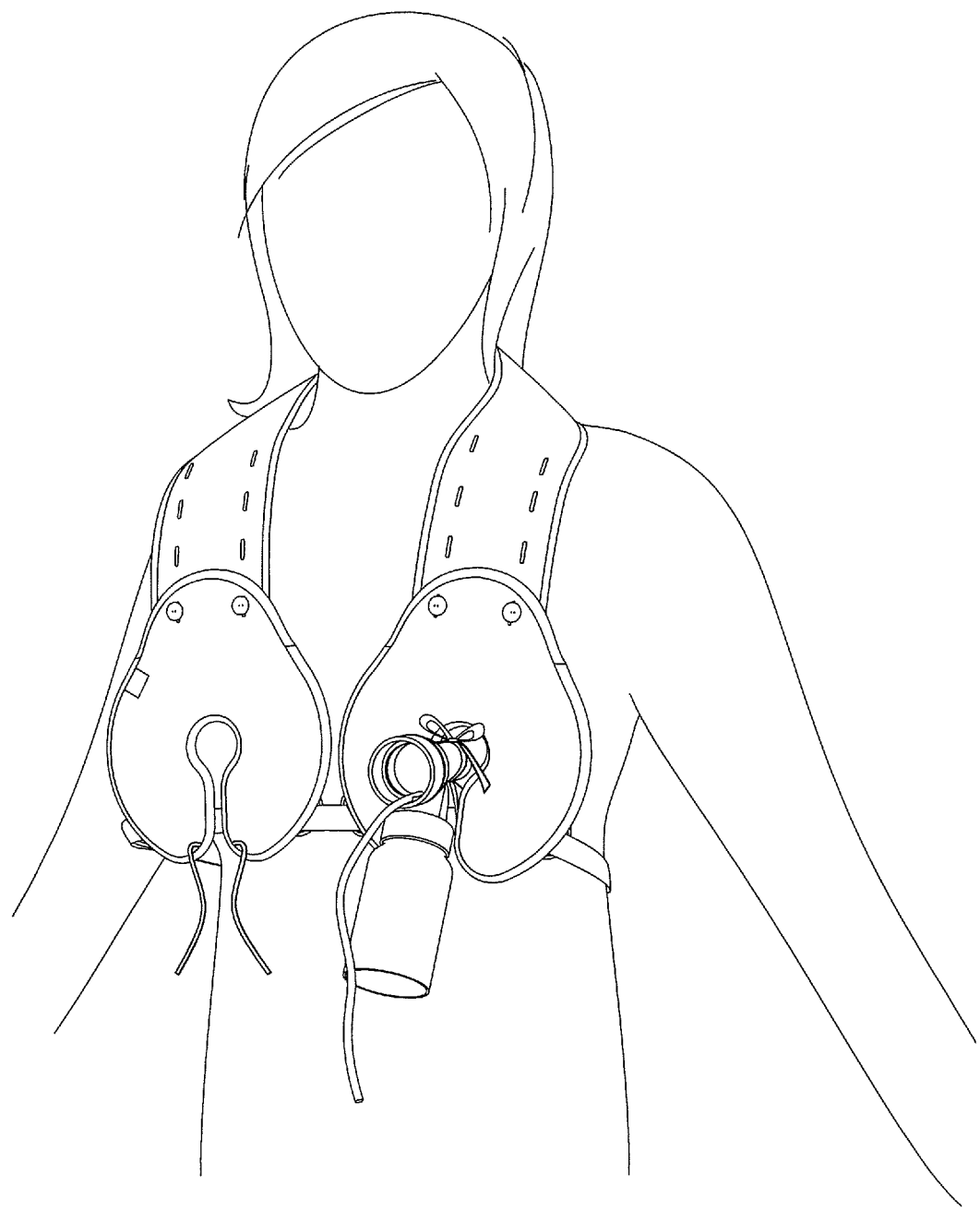
FIG. 29 is a perspective view of a lactation aid and soothing garment with third embodiment cozy covers in use with one side attached to a breast pump.
Figure 30:
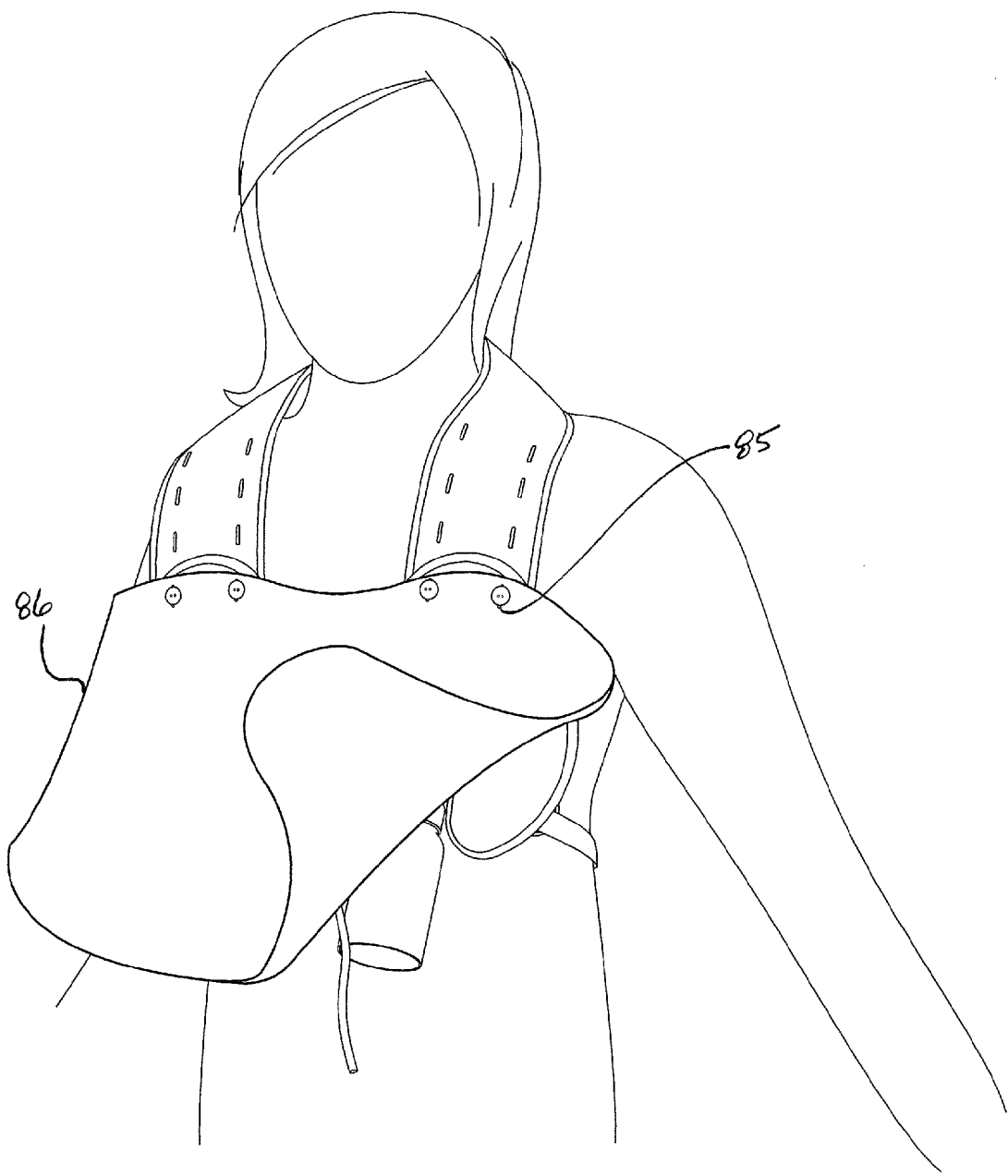
FIG. 30 is a perspective view of a lactation aid and soothing garment in use with the privacy shield attached.

Third embodiment cozy cover 62 is illustrated in FIGS. 34-36. Cozy cover 62 is washable and made of an outer non-contiguous donut shaped fabric half 74 and an inner substantially similar, non-contiguous donut shaped fabric half 76 stitched about a portion of their exterior perimeter to form a pocket capable of retaining third embodiment breast cozy 64, and is made for its sealable retention. As such, cozy cover 62 has a substantially similar keyhole shaped void 65. In additional to retaining all attachment means and fasteners identical to second cozy cover 56 and first embodiment cozy cover 4, third embodiment cozy cover 62 has a pair of fabric loops 78 disposed on opposite sides for receiving engagement by a body belt 80. Additionally, a pair of ties 82 is disposed on a bottom end of cozy cover 62 for helping to secure a breast pump flange 84 in FIG. 27. FIG. 29 illustrates how the third embodiment breast cozy 64 in conjunction with third embodiment cozy cover 62 secured to adjustable neckband 18 are used to secure a breast pump flange 84. Body belt 80 helps secure cozy covers 62 to the user by passing through fabric loops 78, while ties 82 are tied around breast pump flange 84 to secure the pump in place. While the use of fabric loops 78 in conjunction with body belt 80 is illustrated herein, other methods of securing flange 84 to cozy cover 62 could be constructed without departing from the scope of the invention. Should the user desire some privacy, opaque, fabric privacy shield 86 can be secured through the third embodiment cozy covers 62 as illustrated in FIG. 30. Privacy shield 86 has two apertures 85 formed therethrough for mating engagement with garment fasteners 18.

Designed for a clinical setting, second embodiment lactation aid and soothing garment 98 is illustrated in FIGS. 50-54 and should be constructed from a antimicrobial, fluid proof, hypoallergenic, stain resistant, antistatic, and flame resistant material such as polyurethane laminate fabric or a coated nylon, which are both soft to the touch and capable of conforming to the body. The thermal mass for second embodiment lactation aid and soothing garment 98 can be thermal beads, gel pack, gel beads, or clay. Clinical breast cozies 100 are configured in circle or egg-shape thermal mass holding compartments, each having an inner convex face 102 and an outer convex face 104, with an adjustable length band 106 connecting the two breast cozies 100 as is illustrated in FIG. 50. To allow the user to connect cozies 100 a first fastening means 108 is affixed to a side of first cozy 101, and a second fastening means 110 is affixed to a side of said second breast cozy 103 and is adapted for connection to said first fastening means 108. In FIGS. 50-54 a dome fastener is illustrated as the fastening means, with first cozy 101 having the socket portion of a dome fastener and cozy 103 having the dome portion. It should be noted that a button and loop or hook-and-loop fastening means could also be employed for connecting first cozy 101 with second cozy 103 without departing from the scope of the invention.

Figure 58:
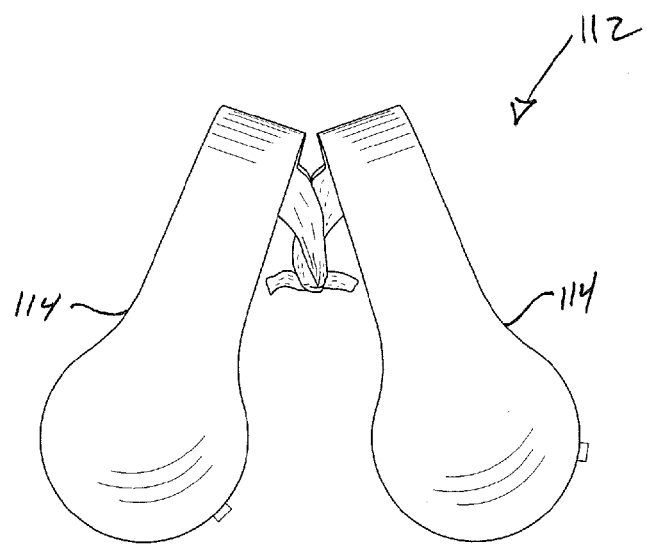
FIG. 58 is a front view of a third embodiment lactation aid and soothing garment tied to a second third embodiment lactation aid and soothing garment.
Figures 59, 60:
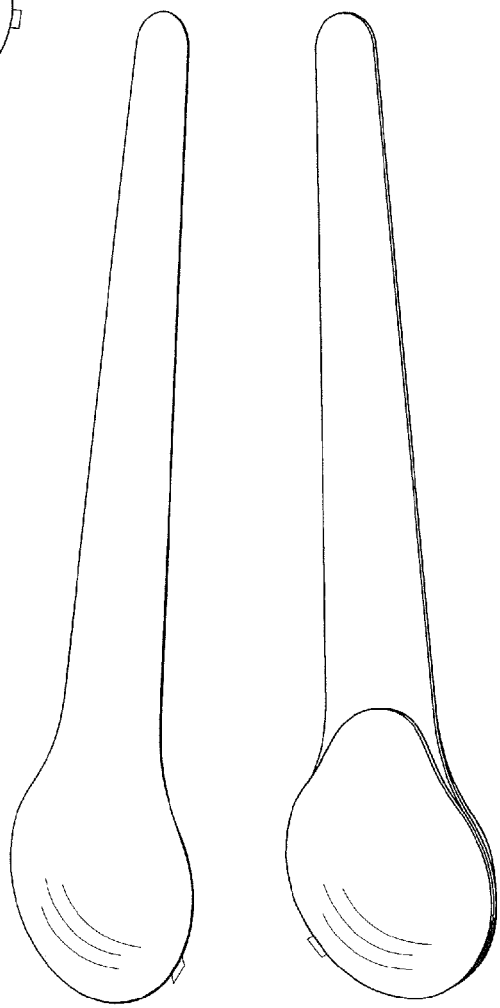
FIG. 59 is a front perspective view of the third embodiment lactation aid and soothing garment.
FIG. 60 is a back perspective view of the third embodiment lactation aid and soothing garment.
Figures 61, 62, 63:
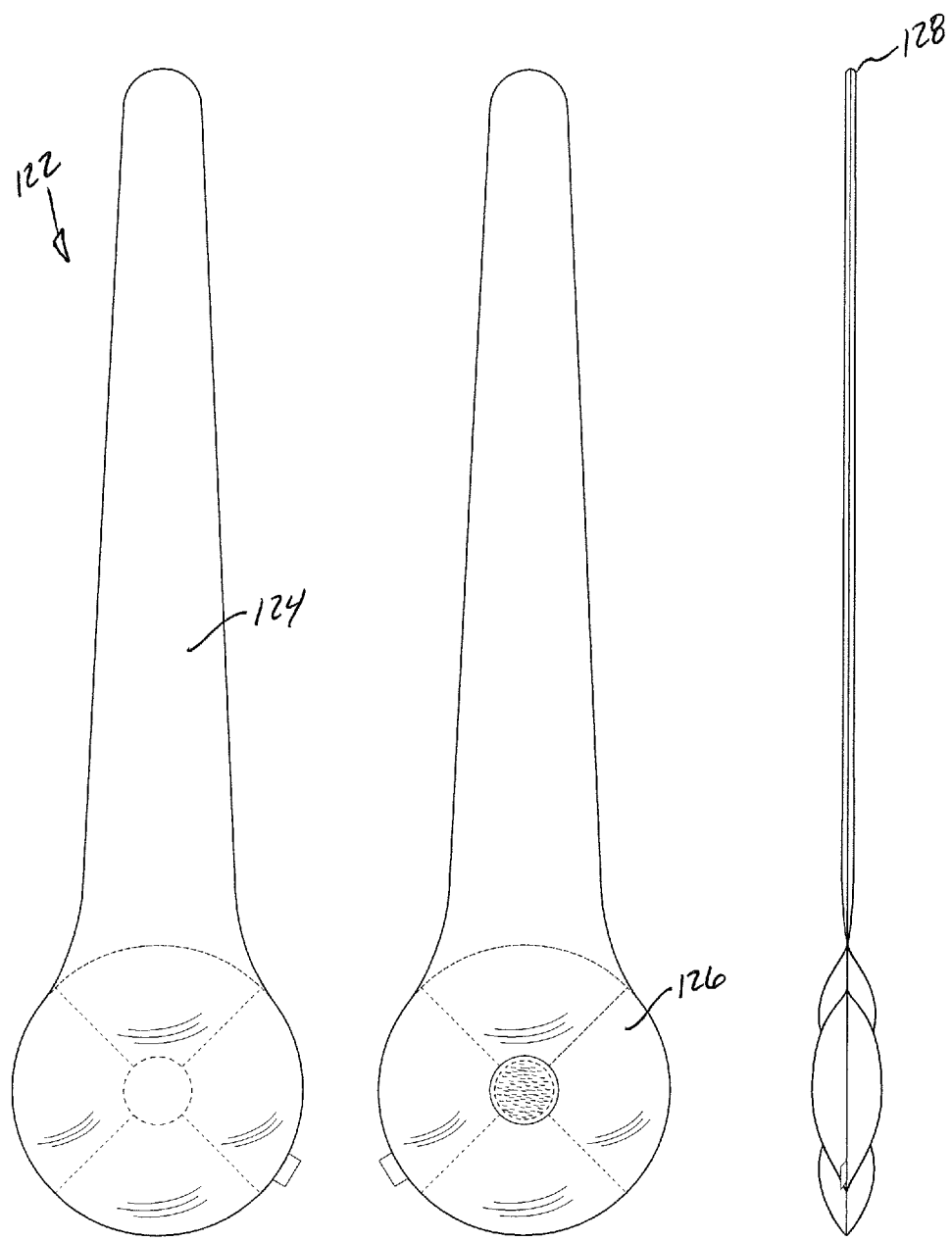
FIG. 61 is a top view of a fourth embodiment lactation aid and soothing garment.
FIG. 62 is a back view of a fourth embodiment lactation aid and soothing garment.
FIG. 63 is a right-side view of a fourth embodiment lactation aid and soothing garment.

A third embodiment lactation aid and soothing garment 112 is illustrated in FIGS. 55-60. Third embodiment lactation aid and soothing garment 112 is comprised two identical attachable slings 114 having a bulbous distal end 116 and a tie-able proximate end 118, and a microwavable and freezeable thermal mass, and is designed to use the breast cozy 10 or 50. Thermal mass container 113 is held via a hook-and-loop fastener within pocket 120 located at bulbous end 116 as is visible in FIG. 57. To use third embodiment lactation aid and soothing garment 112 the user simply places thermal mass container 113, which could be breast cozy 10 or 50, within pockets 120 of two slings 114 and ties the proximate ends together to a desired length as illustrated in FIG. 58 and places the entire assembly into the microwave or freezer to achieve desired temperature.

Finally, fourth embodiment lactation aid and soothing garment 122 is illustrated in FIGS. 61-66. Forth embodiment lactation aid and soothing garment 122 is comprised of two identical attachable slings 124 having a bulbous distal end 126 and a tie-able proximate end 128. Bulbous distal end contains thermal mass of thermal beads which are non toxic, resistant to mold and mildew and washable. The fabric is fast drying synthetic material or as an alternative, natural cotton or a blend. The ends of 128 of the slings 124 are simply tied together to obtain a length of the device that best suits the user.

Although specific embodiments have been illustrated and described herein, it will be appreciated by those of ordinary skill in the art that a wide variety of alternate and/or equivalent implementations calculated to achieve the same purposes may be substituted for the specific embodiment shown and described without departing from the scope of the present invention. Therefore, it is intended that this invention be limited only by the claims and the equivalents thereof.

The invention claimed is:

1. A therapeutic breast garment to be worn over the shoulders and around a user's neck like a scarf, comprising:
   at least one microwavable and freezable breast cozy configured in an egg-shape, having an inner concave face and an outer concave face, with both faces sharing a circular, central stitched region with a series of thermal mass holding compartments radiating out 360° about a perimeter of said central stitched region;
   an aperture (40) formed through said inner concave face and said outer concave face of said cozy near a perimeter joining said inner concave face of said cozy to said outer concave face of said cozy;
   a first one-half mating strip of a hook-and-loop fastener (22) affixed adjacent said aperture (40) on said inner concave face;
   a first means for fastening affixed adjacent said hook-and-loop fastener (22),
   a fastening strap (46) having a proximate end affixed near the perimeter joining said inner concave face of said cozy to said outer concave face of said cozy and a second means for fastening adapted for mating engagement with said first means for fastening affixed to a distal end of said fastening strap,
   wherein said thermal mass holding compartments that radiate out 360° about a perimeter of said central stitched region are defined by stitch lines extending normally from said perimeter of said central stitched region to a stitched circle about the perimeter of said inner concave face and said outer concave face of said cozy;
   wherein said central stitched region further comprises a circular one-half mating strip of hook-and-loop fastener;
   each at least one microwaveable and freezable breast cozy is placed in a washable cozy cover comprising an inner lobe-shaped fabric half cozy cover and an outer lobe-shaped fabric half cozy cover stitched about a portion of their exterior perimeter to form a pocket capable of retaining said cozy, said inner lobe-shaped fabric half cozy cover having at least one garment fastener affixed thereto, and a first aperture and a second aperture formed therethrough said outer lobe-shaped fabric half cozy cover, and a third aperture formed therethrough both said inner lobe-shaped fabric half cozy cover and said outer lobe-shaped fabric half cozy cover adjacent a side perimeter;
   a second one-half mating strip of a hook-and-loop fastener affixed to said inner lobe-shaped fabric half cozy cover for mating engagement with said first one-half mating strip on said inner concave face of said breast cozy;
   an adjustable neck strap having a distal end configured for mating engagement with said at least one garment fastener of a first cozy cover and a proximate end configured for mating engagement with said at least one garment fastener of a second cozy cover;
   wherein said second cozy cover has a pairing strap affixed to a side perimeter thereof, wherein said pairing strap has a distal end connectable to a proximate end of said pairing strap, said pairing strap sized for passing through said third aperture formed therethrough a first cozy cover; and
   the therapeutic breast garment having no fastening strap suitable for securing behind a user's back, and further comprising
   a thermal nipple soother constructed as a polymer disk comprising at least one polymer disk face containing a microwaveable and freezable thermal mass, and
   one-half of a hook-and-loop fastener attached to said at least one polymer disk face of the thermal nipple soother for mating attachment with said circular one-half mating strip of hook-and-loop-fastener of said central stitched region.

2. The therapeutic breast garment of claim 1 further comprising:
   two garment fasteners; and
   at least one connection strap removably connectable to said garment fasteners, so as to form a loop above said top of said cozy cover.

3. A therapeutic breast garment to be worn over the shoulders and around a user's neck like a scarf, comprising:
   at least one microwavable and freezable breast cozy configured in an egg-shape, having an inner concave face and an outer concave face, with both faces sharing a circular, central stitched region with a series of thermal mass holding compartments radiating out 360° about a perimeter of said central stitched region;

an aperture (40) formed through said inner concave face and said outer concave face of said cozy near a perimeter joining said inner concave face of said cozy to said outer concave face of said cozy;

a first one-half mating strip of a hook-and-loop fastener (22) affixed adjacent said aperture (40) on said inner concave face;

a first means for fastening affixed adjacent said hook-and-loop fastener (22), a fastening strap (46) having a proximate end affixed near the perimeter joining said inner concave face of said cozy to said outer concave face of said cozy and a second means for fastening adapted for mating engagement with said first means for fastening affixed to a distal end of said fastening strap, wherein said thermal mass holding compartments that radiate out 360° about a perimeter of said central stitched region are defined by stitch lines extending normally from said perimeter of said central stitched region to a stitched circle about the perimeter of said inner concave face and said outer concave face of said cozy;

wherein said central stitched region further comprises a circular one-half mating strip of hook-and-loop fastener;

each at least one microwaveable and freezable breast cozy is placed in a washable cozy cover comprising an inner lobe-shaped fabric half cozy cover and an outer lobe-shaped fabric half cozy cover stitched about a portion of their exterior perimeter to form a pocket capable of retaining said cozy, said inner lobe-shaped fabric half cozy cover having at least one garment fastener affixed thereto, and a first aperture and a second aperture formed therethrough said outer lobe-shaped fabric half cozy cover, and a third aperture formed therethrough both said inner lobe-shaped fabric half cozy cover and said outer lobe-shaped fabric half cozy cover adjacent a side perimeter;

a second one-half mating strip of a hook-and-loop fastener affixed to said inner lobe-shaped fabric half cozy cover for mating engagement with said first one-half mating strip on said inner concave face of said breast cozy;

an adjustable neck strap having a distal end configured for mating engagement with said at least one garment fasteners of a first cozy cover and a proximate end configured for mating engagement with said at least one garment fasteners of a second cozy cover;

wherein said second cozy cover has a pairing strap affixed to a side perimeter thereof, wherein said pairing strap has a distal end connectable to a proximate end of said pairing strap, said pairing strap sized for passing through said third aperture formed therethrough a first cozy cover; and the therapeutic breast garment having no fastening strap suitable for securing behind a user's back, and further comprising a thermal nipple soother constructed as a fabric disk comprising at least one fabric disk face containing a microwaveable and freezable thermal mass; and one-half of a hook-and-loop fastener attached to said at least one fabric disk face of the thermal nipple soother for mating attachment with said circular one-half mating strip of hook-and-loop fastener of said central stitched region.

4. The therapeutic breast garment of claim 3 further comprising:

two garment fasteners; and at least one connection strap removably connectable to said garment fasteners, so as to form a loop above said top of said cozy cover.

\* \* \* \* \*